(12) United States Patent
Ni

(10) Patent No.: US 12,194,300 B1
(45) Date of Patent: Jan. 14, 2025

(54) MANAGING OBSTRUCTIVE SLEEP APNEA THROUGH UPPER AIRWAY DUAL NEUROSTIMULATION

(71) Applicant: Restora Medical, Inc., Irvine, CA (US)

(72) Inventor: Quan Ni, Irvine, CA (US)

(73) Assignee: Restora Medical, Inc., Irvine, CA (US)

( * ) Notice: Subject to any disclaimer, the term of this patent is extended or adjusted under 35 U.S.C. 154(b) by 0 days.

(21) Appl. No.: 18/742,859

(22) Filed: Jun. 13, 2024

Related U.S. Application Data

(60) Provisional application No. 63/519,463, filed on Aug. 14, 2023.

(51) Int. Cl.
*A61N 1/36* (2006.01)

(52) U.S. Cl.
CPC ........ *A61N 1/3611* (2013.01); *A61N 1/36135* (2013.01); *A61N 1/36146* (2013.01)

(58) Field of Classification Search
CPC .............. A61N 1/3611; A61N 1/36135; A61N 1/36146; A61B 5/0825; A61B 5/0538; A61B 5/1107; A61B 5/4818; A61B 5/4836; A61B 5/486
See application file for complete search history.

(56) References Cited

U.S. PATENT DOCUMENTS

| 9,339,651 B2 | 5/2016 | Meadows et al. | |
| 2011/0093032 A1* | 4/2011 | Boggs, II | ............. A61N 1/3611 607/42 |
| 2022/0032052 A1 | 2/2022 | Kent | |
| 2022/0379114 A1 | 12/2022 | Kent | |
| 2023/0172479 A1 | 6/2023 | Verzal et al. | |
| 2024/0252824 A1* | 8/2024 | Verzal | ................. A61N 1/3611 |

FOREIGN PATENT DOCUMENTS

| WO | 2021242633 A1 | 12/2021 |
| WO | 2022246320 A1 | 11/2022 |
| WO | WO-2024145251 A1 * | 7/2024 |

OTHER PUBLICATIONS

International Search Report and Written Opinion for International patent application No. PCT/US2024/033866, filed Jun. 13, 2024 mailed Sep. 17, 2024.

* cited by examiner

*Primary Examiner* — Brian T Gedeon
(74) *Attorney, Agent, or Firm* — Faegre Drinker Biddle & Reath LLP

(57) ABSTRACT

At least some embodiments of the present disclosure are directed to systems and methods for managing sleep disordered breathing (e.g., obstructive sleep apnea) for a patient. A first implantable electrode delivers a first stimulation signal proximate to a first nerve of the patient to stimulate the first nerve and activate at least one first muscle for an upper airway dilation of the person. A second implantable electrode delivers a second stimulation signal proximate to a second nerve to stimulate the second nerve and activate at least one second muscle for a caudal tracheal traction for an upper airway of the person. A stimulation signal generator generates the first and second stimulation signals and coordinates the delivery of the first stimulation signal with the delivery of the second stimulation signal.

30 Claims, 14 Drawing Sheets

MANAGING OBSTRUCTIVE SLEEP APNEA THROUGH UPPER AIRWAY DUAL NEUROSTIMULATION

CROSS-REFERENCE TO RELATED PATENT APPLICATIONS

This application claims priority to U.S. Provisional Application No. 63/519,463, filed on Aug. 14, 2023, the disclosure of which is hereby incorporated herein by reference in its entirety.

BACKGROUND

Obstructive sleep apnea (OSA) is a common sleep-related breathing disorder. OSA may occur when the muscles in the back of the throat relax during sleep, causing a partial or complete blockage of the airway. Typical treatment options may include positive airway pressure (PAP) therapy using devices like continuous positive airway pressure (CPAP) to help keep the airway open during sleep, and oral appliances using custom-made mouthpieces to reposition the jaw and tongue to prevent airway collapse.

SUMMARY

Certain embodiments of the present disclosure relate to medical systems, apparatus, and methods for managing sleep disordered breathing (e.g., obstructive sleep apnea) in a patient. More specifically, some embodiments of the present disclosure relate to medical systems, apparatus, and methods for managing obstructive sleep apnea in a patient through upper airway dual neurostimulation.

According to some embodiments, a system for managing obstructive sleep apnea for a person includes a first implantable electrode configured to deliver a first stimulation signal proximate to a first nerve of the person to stimulate the first nerve and activate at least one first muscle for an upper airway dilation of the person; a second implantable electrode configured to deliver a second stimulation signal proximate to a second nerve to stimulate the second nerve and activate at least one second muscle for a caudal tracheal traction for an upper airway of the person; and a stimulation signal generator configured to deliver the first stimulation signal to the first implantable electrode, and deliver the second stimulation signal to the second implantable electrode. The first stimulation signal has a series of first stimulation cycles each including a first stimulation period and a first non-stimulation period, the second stimulation signal having a series of second stimulation cycles each including a second stimulation period and a second non-stimulation period, the delivery of the first stimulation signal being coordinated with the delivery of the second stimulation signal. The second stimulation signal is modulated to activate the at least one second muscle within a strain range between a first strain value and a second strain value, wherein a first stimulation level of the second stimulation signal corresponds to the first strain value, and a second stimulation level of the second stimulation signal corresponds to the second strain value.

According to certain embodiments, a method for managing obstructive sleep apnea for a person includes providing a first implantable electrode configured to deliver a first stimulation signal proximate to a first nerve to stimulate the first nerve and activate at least one first muscle for upper airway dilation; providing a second implantable electrode configured to deliver a second stimulation signal proximate to a second nerve to stimulate the second nerve and activate at least one second muscle for a caudal tracheal traction for an upper airway of the person; modulating the second stimulation signal to activate the at least one second muscle within a strain range between a first strain value and a second strain value, where a first stimulation level of the second stimulation signal corresponds to the first strain value, and a second stimulation level of the second stimulation signal corresponds to the second strain value; delivering the first stimulation signal to the first implantable electrode; and delivering the second stimulation signal to the second implantable electrode. The first stimulation signal and the second stimulation signal are coordinated. The first stimulation signal has a series of first stimulation cycles each including a first stimulation period and a first non-stimulation period, the second stimulation signal has a series of second stimulation cycles each including a second stimulation period and a second non-stimulation period.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1A:
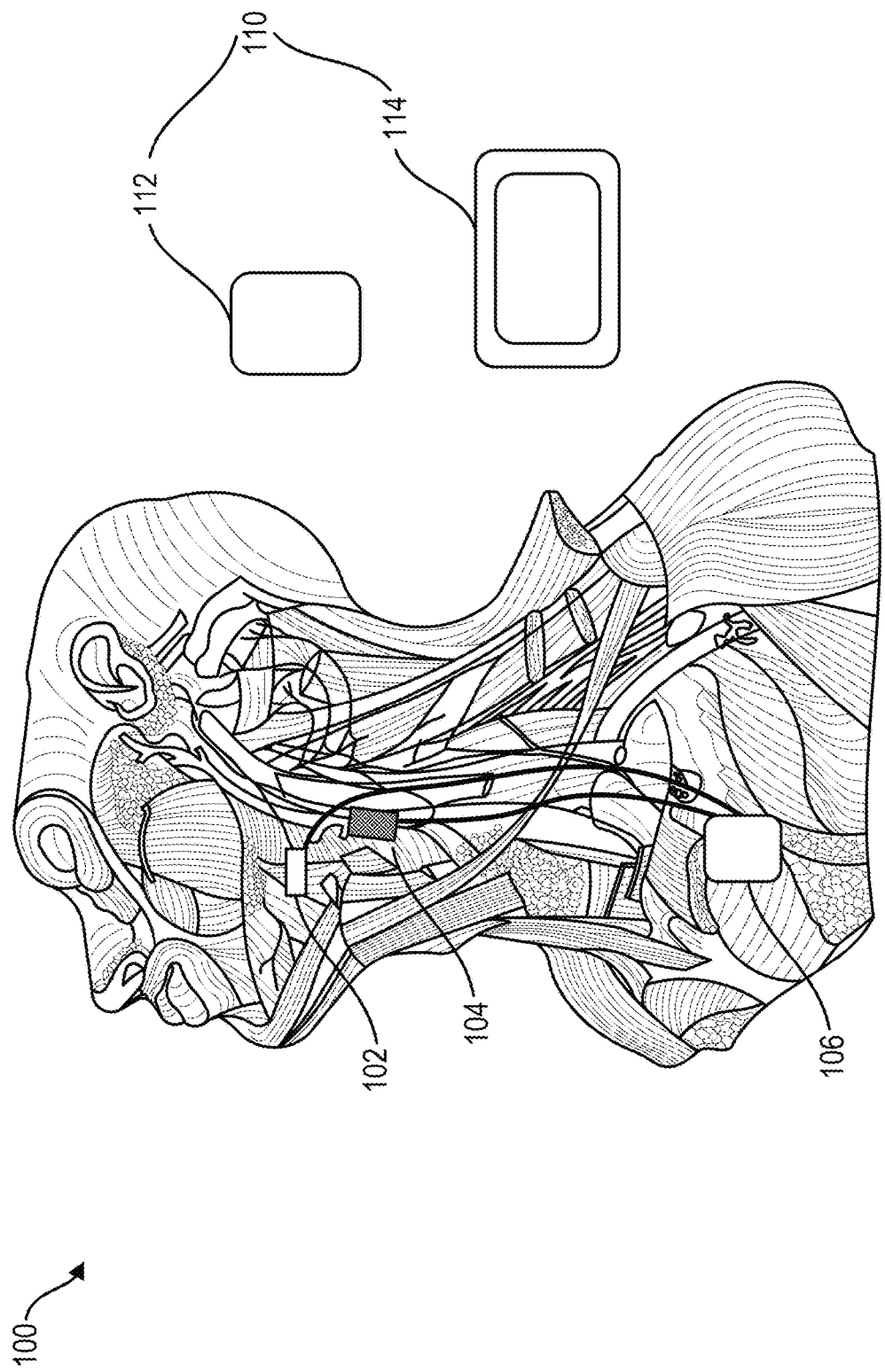
FIG. 1A illustrates a schematic diagram representing patient anatomy and an example medical system for upper airway dual neurostimulation, in accordance with embodiments of the present disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

The following detailed description is exemplary in nature and is not intended to limit the scope, applicability, or configuration of the disclosure in any way. Rather, the following description provides some practical illustrations for implementing exemplary embodiments of the present disclosure. Examples of constructions, materials, and/or dimensions are provided for selected elements. Those skilled in the art will recognize that many of the noted examples have a variety of suitable alternatives.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g., 1 to 5 includes 1, 1.5, 2, 2.75, 3, 3.80, 4, and 5) and any number within that range.

Although illustrative methods may be represented by one or more drawings (e.g., flow diagrams, communication flows, etc.), the drawings should not be interpreted as implying any requirement of, or particular order among or between, various steps disclosed herein. However, some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information. In some embodiments, the term "receive" or "receiving" means obtaining from a data repository (e.g., database), from another system or service, from another software, or from another software component in a same software. In certain embodiments, the term "access" or "accessing" means retrieving data or information, and/or generating data or information.

Typical treatment options for obstructive sleep apnea (OSA) in a patient such as positive airway pressure (PAP) therapy may not be suitable for many patients. Hypoglossal nerve stimulation (HNS) is considered as an effective form of therapy for patients with OSA for whom PAP therapy is not suitable. In a typical method for stimulating airway patency-related tissue using hypoglossal nerve stimulation (HNS), an implanted neurostimulator is used to generate stimulation signals to deliver to an implanted stimulation lead based on respiratory information of the patient sensed by a sensing lead. Hypoglossal nerve stimulation (HNS) therapy can work by protruding and stiffening the tongue muscle thereby reducing obstruction from the tongue. However, HNS therapy may not reduce obstruction from the lateral wall. It was found that about 35% implanted patients do not respond to the hypoglossal nerve stimulation (HNS). For example, it was found that patients with lateral wall collapse had a reduced response to HNS. As such, ways to improve treatment for OSA are needed. At least some embodiments of the present disclosure are directed to medical systems, devices, and methods for managing obstructive sleep apnea in a patient through upper airway dual neurostimulation.

FIG. 1A illustrates a schematic diagram representing patient anatomy and a system 100 for upper airway dual neurostimulation for a person, in accordance with embodiments of the present disclosure. The system 100 includes a first implantable electrode 102 configured to deliver a first stimulation signal proximate to a first nerve of the person to stimulate the first nerve and activate at least one muscle for an upper airway dilation of the person. In some embodiments, the system 100 further includes a second implantable electrode 104 configured to deliver a second stimulation signal proximate to a second nerve to stimulate the second nerve and activate at least one muscle for a caudal tracheal traction for an upper airway of the person.

In some embodiments, the system 100 further includes a stimulation signal generator 106 configured to deliver the first stimulation signal to the first implantable electrode 102 and deliver the second stimulation signal to the second implantable electrode 104. The stimulation signal generator 106 can be positioned (e.g., implanted) in any suitable locations and be connected to the implantable electrodes 102 and 104 wirelessly or via wires. In some embodiments, the stimulation signal generator 106 is implanted in or on a patient's body, for example, in the chest, adjacent to the implantable electrodes 102 and 104. In some embodiments, the implantable electrodes 102 and 104 can be operably coupled to the same, single stimulation signal generator 106. In some embodiments, the stimulation signal generator 106 can include a first stimulation signal generator coupled to the first implantable electrode 102 and a second stimulation signal generator coupled to the second implantable electrode 104. The first and second stimulation signal generators can be disposed within the same physical housing or separate housings.

According to certain embodiments, the stimulation signal generator 106 can be controlled to generate one or more stimulation signals and deliver the generated stimulation signals to one or more electrodes. In some embodiments, the stimulation signal generator 106 can be controlled to convey various patterns of electrical currents and voltages to generate the stimulation signals.

In some embodiments, the stimulation signal generator 106 can generate a first stimulation signal having a first set of stimulation parameters, and a second stimulation signal having a second set of stimulation parameters. In certain embodiments, the first stimulation signal has a series of first stimulation cycles each including a first stimulation period and a first non-stimulation period. In some embodiments, the second stimulation signal has a series of second stimulation cycles each including a second stimulation period and a second non-stimulation period.

In some embodiments, the stimulation signal generator 106 can be a pulse generator to generate a series of pulses in the stimulation period of each stimulation cycle. The stimulation signal generator 106 can control the one or more stimulation parameters of the pulse signal, including one or more of an amplitude, a frequency, a pulse width, a rate of amplitude change, a duty cycle, and the like.

In some embodiments, the stimulation signal generator 106 can coordinate the delivery of the first stimulation signal with the delivery of the second stimulation signal. In certain embodiments, the stimulation signal generator 106 includes an internal timer to provide timing for the series of first stimulation cycles of the first stimulation signal and the series of second stimulation cycles of the second stimulation signal. In some embodiments, the internal timer can synchronize the first stimulation periods and the first non-stimulation periods of the first stimulation signal with the second stimulation periods and the second non-stimulation periods of the second stimulation signal, respectively.

In some embodiments, the system 100 further includes a remote controller 110 functionally connected to the stimulation signal generator 106 to control operation of the stimulation signal generator. In some embodiments, the remote controller 110 is configured to control or adjust one or more stimulation parameters for the stimulation signal generator 106 including, for example, a duration of stimulation cycle, a duration of a stimulation period, a duration of a non-stimulation period, a coordination between a first stimulation signal and a second stimulation signal, a pulse amplitude, a pulse frequency, a pulse width, a duty cycle of the generated stimulation signal, and the like. In some embodiments, the controller 110 allows a user to adjust a first amplitude of the first stimulation signal and a second amplitude of the second stimulation signal to obtain an optimized combination of the first amplitude and the second amplitude.

In the embodiment depicted in FIG. 1A, the remote controller 110 includes a first controller 112 and a second controller 114. In some embodiments, the first controller 112 can be a patient remote controller for a patient to control operation of the stimulation signal generator 106. For example, the patient can use the controller to turn on or turn off the stimulation signal generator 106, to adjust the respective amplitudes of one or more stimulation signals, to switch the operation of the stimulation signal generator 106 between a first mode and a second mode, and the like. In some embodiments, the controller 110 can automatically turn on or off the stimulation signal generator 106 based on the time of day. In some embodiments, the second controller 114 can be a clinician programming device for a physician or clinician to adjust one or more stimulation parameters for the stimulation signal generator 106.

In some embodiments, the first implantable electrode 102 is configured to deliver the first stimulation signal proximate to a hypoglossal nerve to stimulate the hypoglossal nerve and activate at least one tongue muscles. In some embodiments, the second implantable electrode 104 is configured to deliver a second stimulation signal proximate to an ansa cervicalis nerve to stimulate the ansa cervicalis nerve and activate at least one infrahyoid muscle.

Figure 1B:
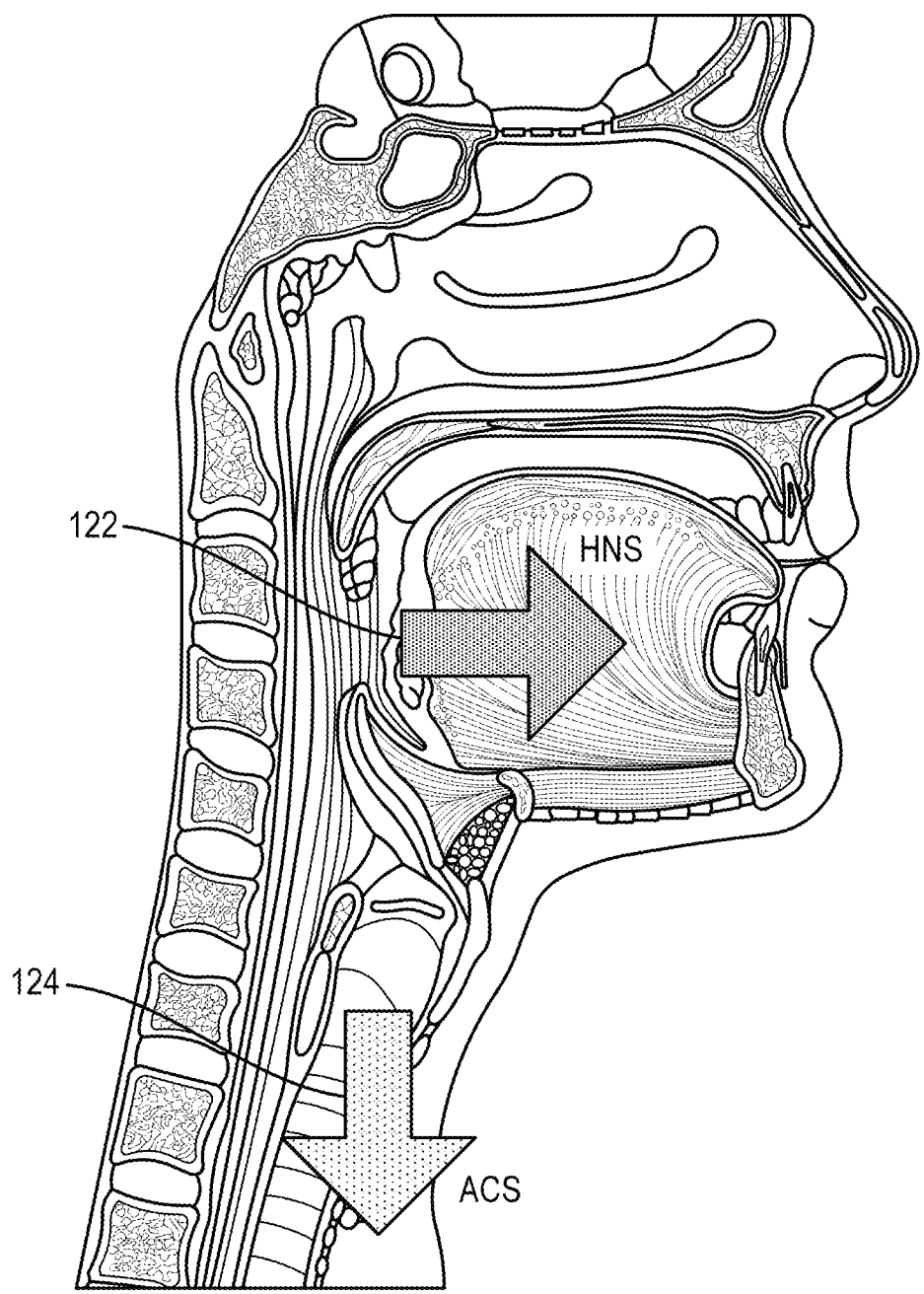
FIG. 1B illustrates a schematic diagram representing the patient anatomy of FIG. 1A.

FIG. 1B illustrates a schematic diagram representing the patient anatomy of FIG. 1A showing a treatment effect through upper airway dual neurostimulation. In some embodiments, the first stimulation signal is delivered to activate one or more protrusor muscles of the tongue (e.g., genioglossus) to displace tongue base anteriorly as indicated by arrow 122 of FIG. 1B for hypoglossal nerve stimulation (HNS), which can pull soft palate anteriorly and stiffen the pharyngeal lateral wall antero-posteriorly. In some embodiments, the second stimulation signal is delivered to activate one or more infrahyoid muscles to descend a hyoid-thyroid complex, which results in a trachea caudal traction that stiffens the pharyngeal lateral wall and posterior wall inferiorly as indicated by arrow 124 of FIG. 1B for ansa cervicalis nerve stimulation (ACS).

Figure 2:
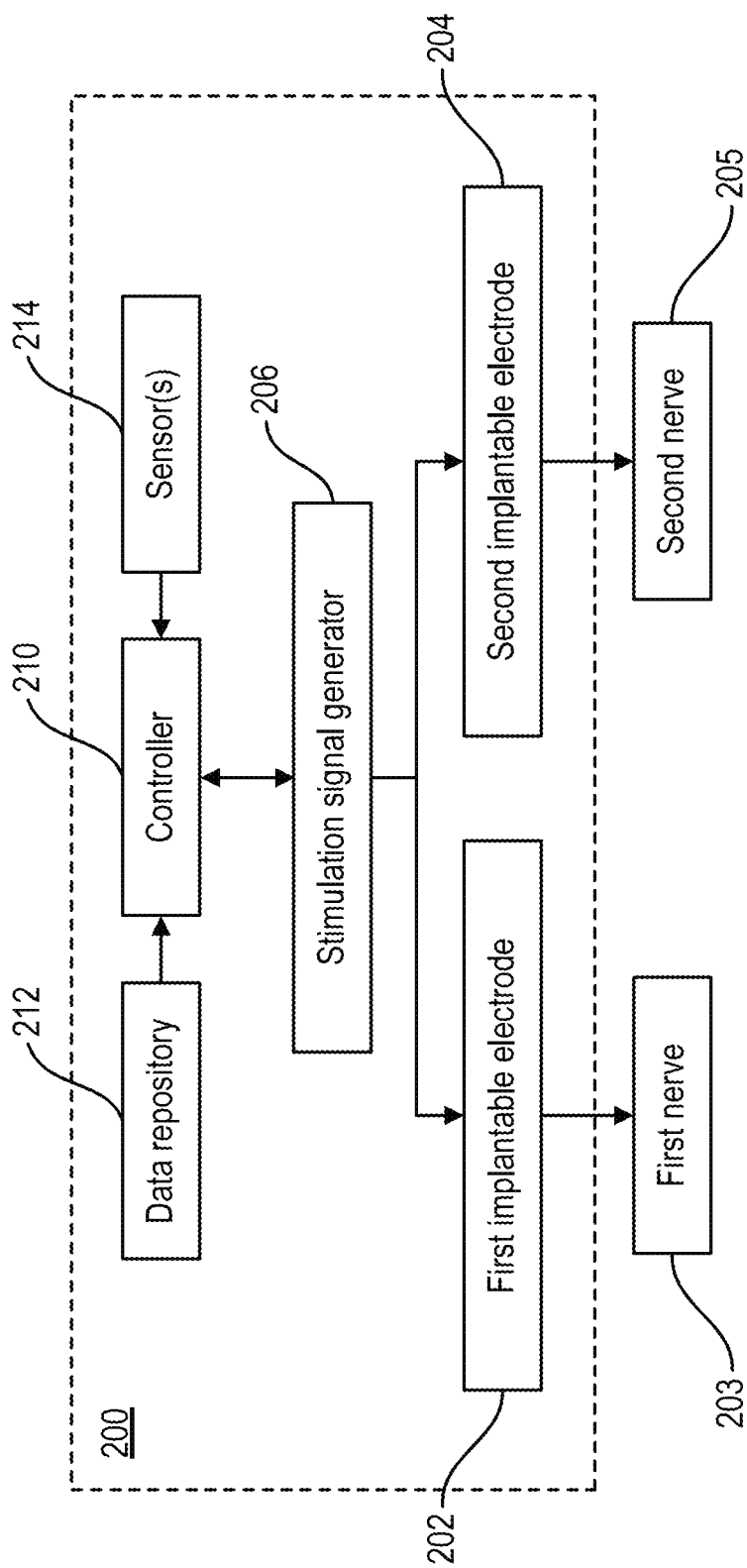
FIG. 2 is a block diagram of an example medical system for managing obstructive sleep apnea of a patient through upper airway dual neurostimulation, in accordance with embodiments of the present disclosure.

FIG. 2 is a block diagram of a medical system 200 for managing obstructive sleep apnea in a patient through upper airway neurostimulation, in accordance with embodiments of the present disclosure.

In some embodiments, the medical system 200 includes a first implantable electrode 202 configured to deliver a first stimulation signal proximate to a first nerve 203 of the person to stimulate the first nerve 203, a second implantable electrode 204 configured to deliver a second stimulation signal proximate to a second nerve 205.

In some embodiments, the first implantable electrode 202 is configured to deliver the first stimulation signal proximate to a hypoglossal nerve to stimulate the hypoglossal nerve and activate at least one tongue muscle. In some embodiments, the second implantable electrode 204 is configured to deliver a second stimulation signal proximate to an ansa cervicalis nerve to stimulate the ansa cervicalis nerve and activate at least one infrahyoid muscle. In some embodiments, the medical system 200 can include a third implantable electrode configured to deliver a third stimulation signal proximate to a third nerve to stimulate the third nerve. The third nerve can be, for example, a phrenic nerve.

In some embodiments, the medical system 200 further includes a stimulation signal generator 206 configured to deliver the first stimulation signal to the first implantable electrode 202 and deliver the second stimulation signal to the second implantable electrode 204. The first stimulation signal has a series of first stimulation cycles including a first stimulation period and a first non-stimulation period. The second stimulation signal has a series of second stimulation cycles including a second stimulation period and a second non-stimulation period. The delivery of the first stimulation signal is coordinated with the delivery of the second stimulation signal.

In some embodiments, the stimulation signal generator 206 can include one or more pulse generators each configured to generate a stimulation signal including a series of stimulation cycles including a stimulation period and a non-stimulation period. A stimulation period of a stimulation cycle can include a series of stimulation pulses having one or more pulse parameters. Example pulse parameters include a pulse frequency, an amplitude, a pulse width, a duty cycle, and the like. A pulse frequency can be, for example, from about 5 Hz to about 40 Hz (e.g., at or about 30 Hz). A pulse width can be, for example, from about 10 microseconds to about 1000 microseconds (e.g., at or about 100 microseconds). A duty cycle can refer to a percentage of a duration of stimulation at a pulse amplitude to a duration of a stimulation cycle (e.g., the sum of a duration of stimulation and a duration of no stimulation). A duration of a stimulation cycle can be, for example, in the range from 2 seconds to 10 minutes. A duty cycle can be, for example, in a range from about 5 percent to 95 percent. A pulse amplitude may refer to the difference between a higher voltage level and a lower voltage level. A pulse amplitude can be, for example, in the range from 0.1 to 15 volts or 0.1 to 15 mA.

In some embodiments, the medical system 200 further includes a controller 210 functionally connected to the stimulation signal generator 206 to control operation of the stimulation signal generator. In some embodiments, the controller 210 is a remote controller configured to control one or more stimulation parameters for the stimulation signal generator 106 including, for example, one or more of an amplitude, a frequency, a pulse width, a rate of amplitude change, a duty cycle, and the like, of the generated stimulation signal.

In some embodiments, the controller 210 can include a patient remote controller for a patient to control operation of the stimulation signal generator 206 including, for example, to turn on or off the stimulation signal generator 206, to adjust the respective amplitudes of one or more stimulation signals, to switch the operation of the stimulation signal generator 106 from a first mode to a second mode, and the like.

In some embodiments, the controller 210 can include a clinician programming device for a physician or clinician to pre-program the stimulation signal generator 206 with desired stimulation parameters. The stimulation parameters can be controllable to allow one or more stimulation signals be remotely modulated to desired settings without removal of the corresponding electrodes from their target positions.

In some embodiments, the controller 210 can include one or more computing devices each of which can include a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices.

In some embodiments, the medical system 200 further includes one or more sensors 214. In certain embodiments, the sensors 214 can be external sensors configured to detect one or more physiological information of the patient, including, for example, the apnea-hypopnea index (AHI), the oxygen desaturation index (ODI), the respiratory disturbance index (RDI), a posture change, a sleep stage, a body motion for restlessness, and the like. It is to be understood that the external sensors can be any suitable type of sensors including, for example, an acoustic sensor for snoring detection. In some embodiments, apnea-hypopnea index (AHI) refers to a measure of the number of times a person or patient has upper airway obstruction during sleep. For example, an AHI of five to fifteen can be a mild sleep apnea. The patient's AHI can be monitored by using any suitable sensors/devices. Similarly, ODI and RDI measures oxygen saturation and respiratory flow changes resulted from upper airway obstruction associated with sleep apnea.

According to certain embodiments, the sensors 214 can generate a sensor signal based on the physiological parameters or changes and send the sensor signal to the controller 210. The controller 210 can process the sensor signal and control/adjust one or more stimulation parameters of the stimulation signal generator 206 based, at least in part, on the one or more physiological parameters. In some examples, the sensors 214 can include a position sensor to sense body position or posture during sleep. In some examples, the sensors 214 can determine a sleep stage, for example, whether the patient is in a deep sleep or a shallow sleep. In some examples, multiple sensors can be combined to measure the patient's AHI during sleep.

In some embodiments, the sensors 214 can send the related sensing data to the controller 210 to determine whether a patient is entering a stable sleep. When the controller 210 determines that the patient is entering a stable sleep, the controller 210 can retrieve a stored therapy setting from the data repository and send the therapy setting to the stimulation signal generator 206 to adjust the corresponding one or more first stimulation parameters of the first stimulation signal and/or one or more first stimulation parameters of the second stimulation signal.

In some embodiments, the sensors 214 can send the related sensing data to the controller 210 to determine whether a patient is turning to a supine posture. When the controller 210 determines that the patient is turning to a supine posture, the controller 210 can retrieve a stored therapy setting from the data repository and send the therapy setting to the stimulation signal generator 206 to adjust the corresponding one or more first stimulation parameters of the first stimulation signal and/or one or more first stimulation parameters of the second stimulation signal.

In some embodiments, the sensors 214 can send the related sensing data to the controller 210 to determine whether a patient is having an increased AHI. When the controller 210 determines that the patient is having an increased AHI, the controller 210 can retrieve a stored therapy setting from the data repository and send the therapy setting to the stimulation signal generator 206 to adjust the corresponding one or more first stimulation parameters of the first stimulation signal and/or one or more first stimulation parameters of the second stimulation signal.

In some embodiments, the medical system 200 further includes a data repository 212 to store data for the medical system 200. In some embodiments, the data repository 212 can be implemented using any one of the memory or storage configurations described below. A data repository can include random access memories, flat files, XML files, and/or one or more database management systems (DBMS) executing on one or more database servers or a data center. A database management system can be a relational (RDBMS), hierarchical (HDBMS), multidimensional (MDBMS), object oriented (ODBMS or OODBMS) or object relational (ORDBMS) database management system, and the like. The data repository can be, for example, a single relational database. In some cases, the data repository may include a plurality of databases that can exchange and aggregate data by a data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the medical system 200 can communicate via or be coupled to via a communication network or interface, for example, a wired or wireless network or interface. The communication network or interface can be any suitable communication network or combination of communication networks. For example, communication network can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard), a wired network, and the like. In some examples, communication network can be a local area network (LAN), a wide area network (WAN), a public network (e.g., the Internet), a private or semi-private network (e.g., a corporate or university intranet), any other suitable type of network, or any suitable combination of networks. Communication links (arrows) between components of the medical system 200 can each be any suitable communication link or combination of communication links, such as wired links, fiber optics links, Wi-Fi links, Bluetooth links, cellular links, and the like.

Figure 3:
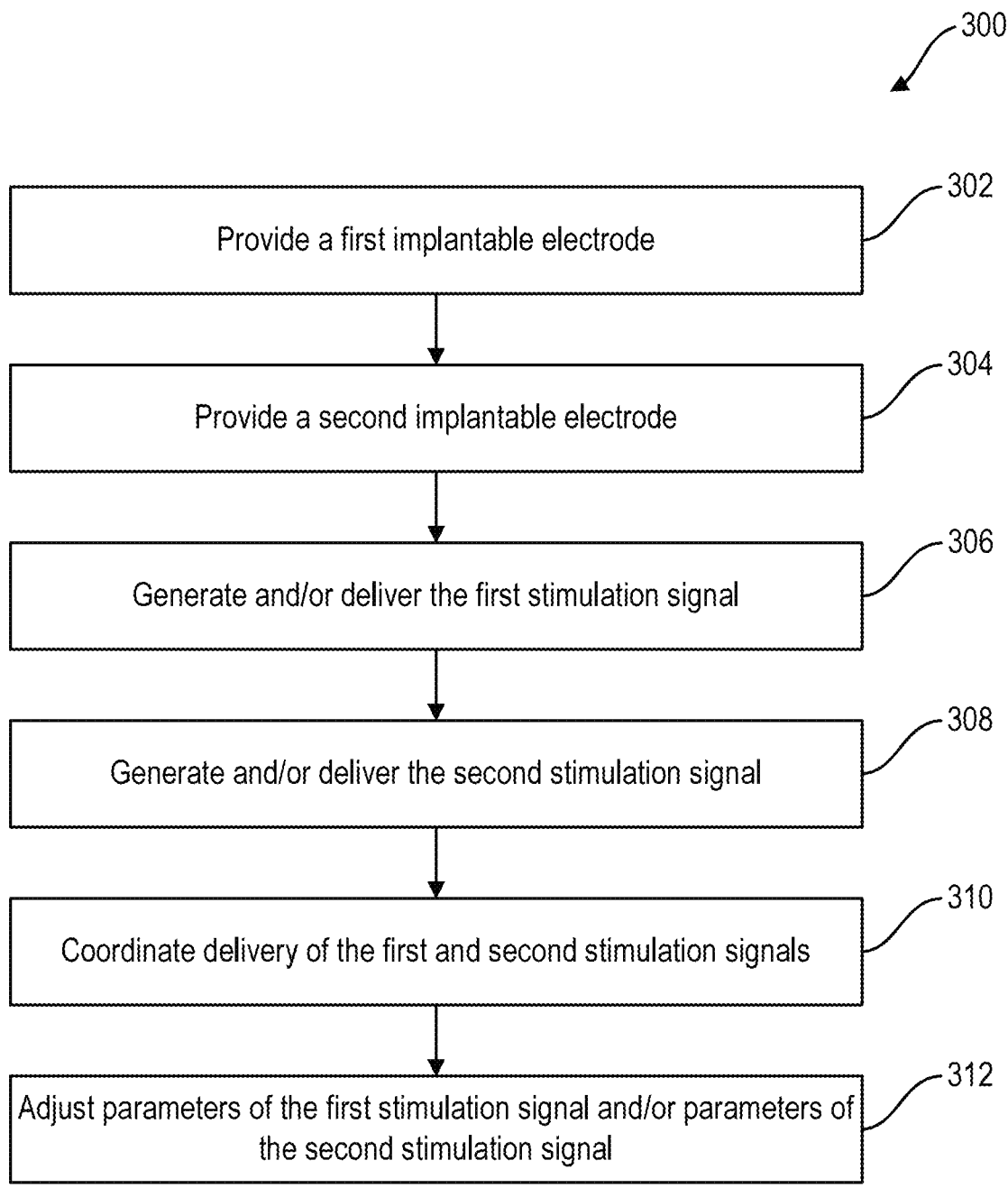
FIG. 3 is an example flow diagram of a medical method for managing obstructive sleep apnea of a patient through upper airway dual neurostimulation, in accordance with embodiments of the present disclosure.

FIG. 3 is a flow diagram of a medical method 300 for managing obstructive sleep apnea (OSA) of a patient through upper airway neurostimulation, in accordance with embodiments of the present disclosure. The method is described in relation to the stimulation signal generators and electrodes discussed previously here. It is to be understood that any stimulation signal generators and electrodes can be used in the method. Aspects of embodiments of the method may be performed, for example, by a medical system or a controller (e.g., the medical system 200 in FIG. 2, the controller 210 in FIG. 2). One or more steps or blocks of method are optional and/or can be modified by one or more steps of other embodiments described herein. Additionally, one or more steps of other embodiments described herein may be added to the method.

According to certain embodiments, at process 302, a first implantable electrode is provided proximate to a first nerve of a patient. In some embodiments, the first implantable electrode can be implanted proximate to the hypoglossal nerve of the patient. In some embodiments, the first implantable electrode can be implanted proximate to one or more medial branches of the hypoglossal nerve (m-XII) to stimulate the one or more medial branches and activate one or more protrusion muscles of the at least one tongue muscle including genioglossus. In some embodiments, the first electrode can be transcutaneously implanted by inserting into a ranine vein of the patient to be placed and fixed proximate to the first nerve, which can be, for example, one or more medial branches of the hypoglossal nerve. In some embodiments, the first electrode can be percutaneously implanted by inserting through the skin and tissue of the patient to be placed and fixed proximate to the first nerve, which can be, for example, one or more medial branches of the hypoglossal nerve. In some embodiments, the nerve can be located proximate to a location that selectively recruits protrusion muscles and reduces recruitment of retraction muscles. In some examples, the first electrode can include one or more percutaneous electrodes, one or more cuff electrodes, one or more wire electrodes, and the like.

According to certain embodiments, at process 304, a second implantable electrode is provided proximate to a second nerve of a patient. In some embodiments, the second implantable electrode can be implanted to stimulate the ansa cervicalis nerve and activate one or more of the infrahyoid muscles including, for example, omohyoid, sternothyroid and sternohyoid muscles, combined muscles of omohyoid, sternothyroid and sternohyoid, or sternothyroid and sternohyoid. In some embodiments, the second implantable electrode can be implanted to deliver the second stimulation signal to stimulate certain nerve branch(es) of the ansa cervicalis and activate sternothyroid and sternohyoid muscles simultaneously. In some embodiments, the second electrode can be transcutaneously implanted by inserting into an internal jugular vein of the patient to placed and fixed to the second nerve to stimulate the ansa cervicalis nerve and activate one or more of the infrahyoid muscles including, for example, omohyoid, sternothyroid and sternohyoid muscles, combined muscles of omohyoid, sternothyroid and sternohyoid, or sternothyroid and sternohyoid. In some embodiments, the second electrode can be percutaneously implanted by inserting through the skin and tissue of the patient to be placed and fixed proximate to the second nerve to stimulate the ansa cervicalis nerve and activate one or more of the infrahyoid muscles including, for example, omohyoid, sternothyroid and sternohyoid muscles, combined muscles of omohyoid, sternothyroid and sternohyoid, or sternothyroid and sternohyoid. In some examples, the second electrode can include one or more percutaneous leads, one or more paddle leads, one or more cuff leads, and the like.

According to certain embodiments, at process 306, the stimulation signal generator 206 generates and/or delivers a first stimulation signal. In some embodiments, the first stimulation signal can include a series of first stimulation cycles including a first stimulation period and a first non-stimulation period. A first stimulation period of a stimulation cycle can include a series of first stimulation pulses having one or more first pulse parameters. Example first pulse parameters include a first pulse frequency, a first pulse amplitude, a first pulse width, a first duty cycle, and the like.

According to certain embodiments, at process 308, the stimulation signal generator 206 generates and/or delivers a second stimulation signal. In some embodiments, the second stimulation signal can include a series of second stimulation cycles each including a second stimulation period and a second non-stimulation period. A second stimulation period of a stimulation cycle can include a series of first stimulation pulses having one or more second pulse parameters. Example second pulse parameters include a second pulse frequency, a second pulse amplitude, a second pulse width, a second duty cycle, and the like.

According to certain embodiments, at process 310, the controller 210 coordinates the delivery of the first stimulation signal through the first implantable electrode proximate to a first nerve and the delivery of the second stimulation signal through the second implantable electrode proximate to a second nerve. In some embodiments, the first nerve is stimulated to activate at least one muscle for an upper airway dilation of the patient. In some embodiments, the second nerve is stimulated to activate at least one muscle for a caudal tracheal traction for an upper airway of the patient. The method 300 proceeds to 312.

According to certain embodiments, at process 312, the controller 210 adjusts one or more first parameters of the first stimulation signal, and one or more second parameters of the second stimulation signal. In some embodiments, the controller 210 can control or adjust one or more stimulation parameters for the stimulation signal generator 206 to generate first and second stimulation signals. The stimulation parameters include, for example, a first/second duration of a first/second stimulation cycle of the first/second stimulation signal, a first/second duration of a first/second stimulation period of the first/second stimulation signal, a first/second duration of a first/second non-stimulation period of the first/second stimulation signal, a coordination between the first stimulation signal and the second stimulation signal, a first/second pulse amplitude of the first/second stimulation signal, a first/second pulse frequency of the first/second stimulation signal, a first/second pulse width of the first/second stimulation signal, a first/second duty cycle of the of the first/second stimulation signal, and the like. In some embodiments, the controller 210 allows a user to adjust a first amplitude of the first stimulation signal and a second amplitude of the second stimulation signal to obtain an optimized combination of the first amplitude and the second amplitude, while maintaining other stimulation parameters for the first and second stimulation signals.

Figure 4A:
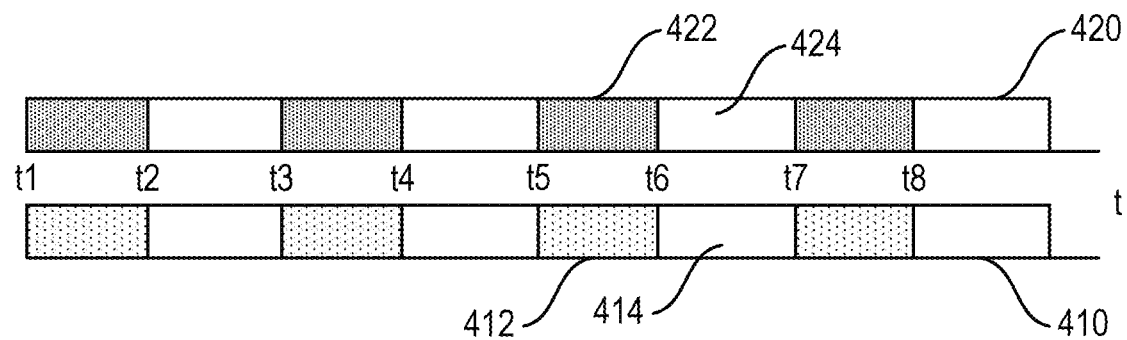
FIG. 4A is a schematic diagram illustrating example timing cycles of dual neurostimulation in a first mode, in accordance with embodiments of the present disclosure.

FIG. 4A is a schematic diagram illustrating example timing cycles of dual neurostimulation in a first mode, in accordance with embodiments of the present disclosure. According to some embodiments, the stimulation signal generator operates in a first mode to synchronize the first stimulation periods and the first non-stimulation periods of the first stimulation signal with the second stimulation periods and the second non-stimulation periods of the second stimulation signal, respectively. As illustrated in the embodiment of FIG. 4A, a first stimulation signal 410 includes a series of stimulation signal cycle each including a first stimulation period 412 and a first non-stimulation period 414. A second stimulation signal 420 includes a series of stimulation signal cycle each including a second stimulation period 422 and a second non-stimulation period 424. In some embodiments, the duration T1_on of the first stimulation period 412 and the duration T2_on of the second stimulation period 422 can be substantially the same. That is, T1_on=T2_on. In some embodiments, the first stimulation signal 410 and the second stimulation signal 420 are substantially synchronized with each other. In some examples, the onset of the first stimulation period 412 and the onset of the second stimulation period 422 can be aligned with each other to occur concurrently (e.g., at t1, t3, t5, t7 . . . in FIG. 4A). In some examples, the onset of the first stimulation period 412 and the onset of the second stimulation period 422 can be aligned with each to have an offset $T_{offset}$. For example, when the onset of the first stimulation period 412 is at t1, the onset of the second stimulation period 422 can be at t1'=t1±$T_{offset}$.

Figure 4B:
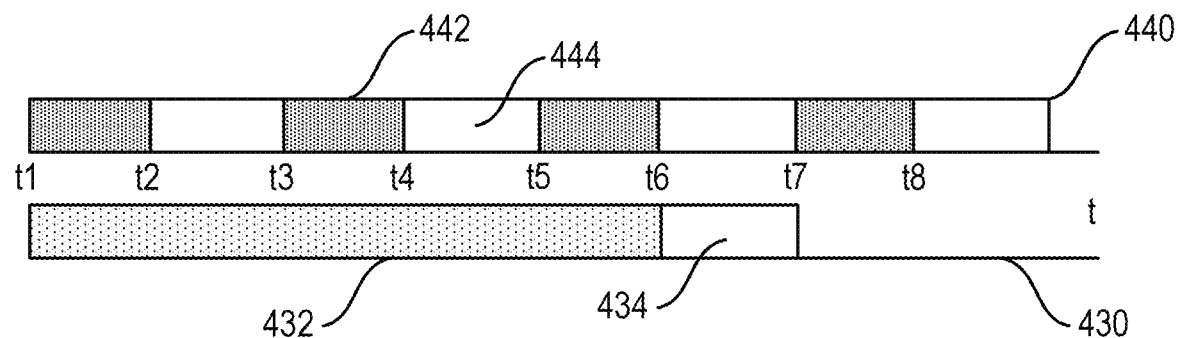
FIG. 4B is a schematic diagram illustrating example timing cycles of dual neurostimulation in a second mode, in accordance with embodiments of the present disclosure.

FIG. 4B is a schematic diagram illustrating example timing cycles of dual neurostimulation in a second mode, in accordance with embodiments of the present disclosure. According to some embodiments, when the stimulation signal generator operates in a second mode, first stimulation signal(s) can be dominant compared to second stimulation signal(s). As illustrated in the embodiment of FIG. 4B, a first stimulation signal 430 includes a series of stimulation signal cycle each including a first stimulation period 432 and a first non-stimulation period 434. A second stimulation signal 440 includes a series of stimulation signal cycle each including a second stimulation period 442 and a second non-stimulation period 444. In some embodiments, the duration T1_on of the first stimulation period 432 can be greater than the duration T2_on of the second stimulation period 442. The ratio of T1_on over T2_on can be in a range, for example, from about 1.0 to about 200.0, from about 1.5 to about 200.0, or from about 2.0 to about 200.0. In one example, T2_on is 3 seconds, and T1_on is 10 minutes or 600 seconds.

In some embodiments, the dominant first stimulation signal(s) can be delivered proximate to a hypoglossal nerve to stimulate the hypoglossal nerve and activate at least one tongue muscle. In certain embodiments, the dominant first stimulation signal can be delivered proximate to one or more medial branches of the hypoglossal nerve (m-XII) to stimulate the one or more medial branches and activate one or more protrusion muscles of the at least one tongue muscle including genioglossus.

In some embodiments, the second stimulation signal(s) can be delivered proximate to an ansa cervicalis nerve to stimulate the ansa cervicalis nerve and activate one or more infrahyoid muscles. In some embodiments, the second stimulation signal(s) can stimulate two or more certain nerve branch(es) of ansa cervicalis simultaneously, for example, to activate sternothyroid and sternohyoid muscles simultaneously. In certain embodiments, the stimulation to activate the tongue protrusion muscles can be longer than the stimulation to activate the infrahyoid muscles since the former may have a less load.

In the embodiment depicted in FIG. 4B, the duration T1_on of the first stimulation period 432 substantially equates the sum of three times of duration T2_on of the second stimulation period 442 and two times of duration T2_off of the second non-stimulation period 444. That is, T1_on=3×T2_on+2×T2_off. In some embodiments, the duration T2_off of the second non-stimulation period 444 is substantially the same as the duration T1_off of the first non-stimulation period 434. The onset of one first stimulation period 432 and the onset T2_on of the second stimulation period 422 can be aligned with each other to occur concurrently (e.g., at t1). The offset of the one first stimulation period 432 of the first stimulation periods is synchronized (e.g., at t6) with an offset of another second stimulation period 442 of the second stimulation periods.

Figure 5A:
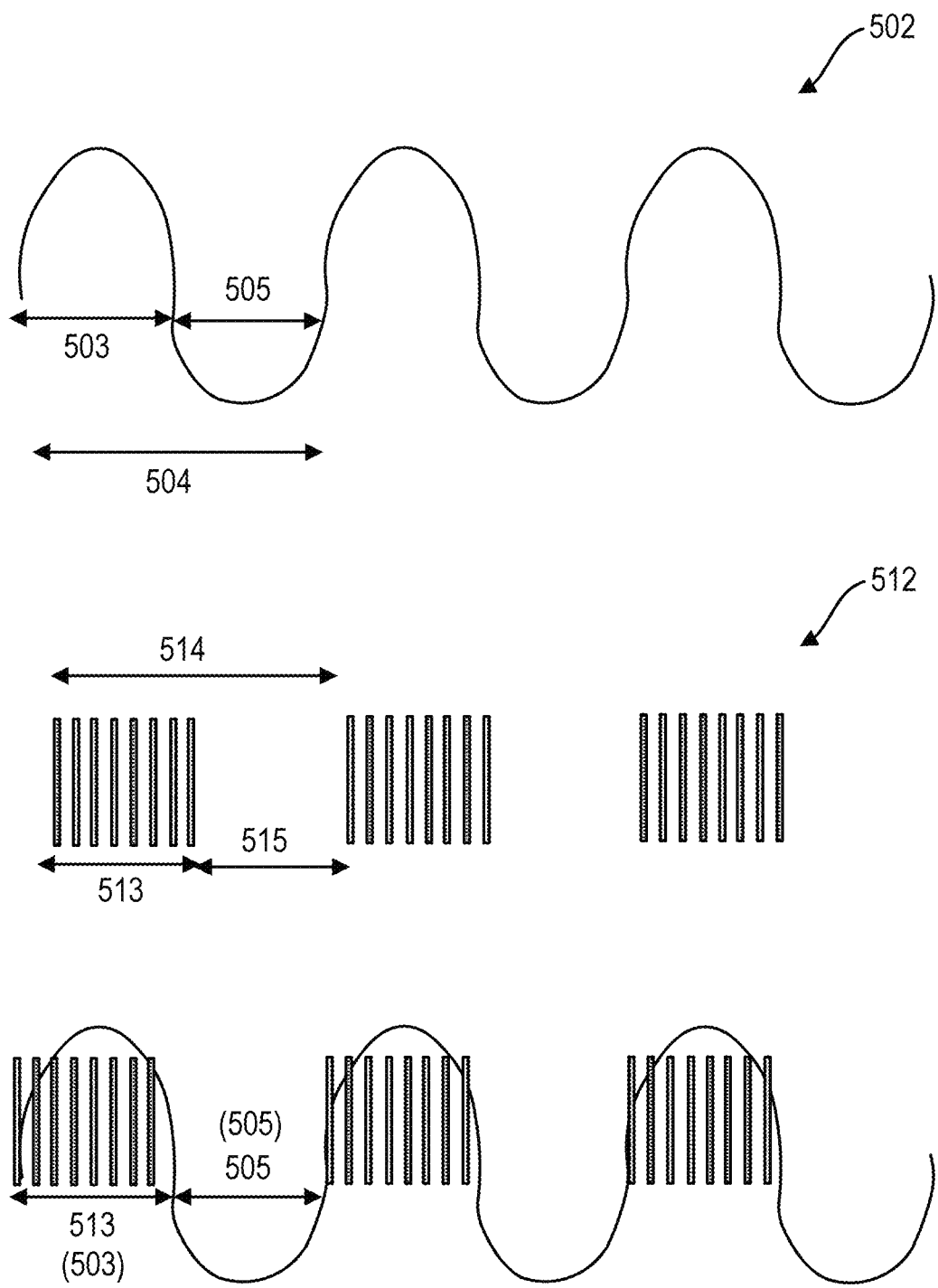
FIG. 5A is a schematic diagram illustrating example neuromodulation entrainment with natural breathing rhythm, in accordance with embodiments of the present disclosure.

FIG. 5A is a schematic diagram illustrating neuromodulation entrainment with natural breathing rhythm, in accordance with embodiments of the present disclosure. The example respiratory waveform 502 includes a series of successively repeated respiratory cycles 504 each including an inspiratory phase 503 and an expiratory phase 505. In some embodiments, the example respiratory waveform 502 can be pre-measured or predetermined for a specific patient. The respiratory waveform 502 can be stored as a historical respiratory waveform in a data repository of a medical system described herein.

In some embodiments, a stimulation signal 512 can include a series of stimulation signal cycles 514 each including a stimulation period 513 and a non-stimulation period 515. In some embodiments, a stimulation signal cycle 514 of the stimulation signal 512 can be controlled or adjusted to have a duration substantially the same as the duration of a respiratory cycle of the historical respiratory waveform 502. For example, the difference between the duration of a stimulation signal cycle 514 of the stimulation signal 512 and the duration of a respiratory cycle 504 of the respiratory waveform 502 can be no great than 20%, no greater than 15%, or no greater than 10%. In some embodiments, the stimulation period 513 can have a duration substantially the same as the duration of the inspiratory phase 503 of the respiratory waveform 502. For example, the difference between the duration of the stimulation period 513 and the duration of the inspiratory phase 503 of the respiratory waveform 502 can be no great than 20%, no greater than 15%, or no greater than 10%. In some embodiments, the non-stimulation period 515 can have a duration substantially the same as the duration of the expiratory phase 505 of the respiratory waveform 502. For example, the difference between the duration of the non-stimulation period 515 and the duration of the expiratory phase 505 of the respiratory waveform 502 can be no great than 20%, no greater than 15%, or no greater than 10%.

In some embodiments, the medical system 200 does not require a sensor to detect the patient's respiratory waveform in real time. Instead, the controller 210 can access the historical respiratory waveform 502 stored in the data repository 212. The controller 210 can determine one or more stimulation parameters based at least in part on the historical respiratory waveform 502. For example, the controller 210 can determine the duration(s) of the stimulation signal 512 based at least in part on the respective duration(s) of the respiratory waveform 502. The controller 210 can send the determined stimulation parameters to the stimulation signal generator 206 to generate and deliver one or more stimulation signals to one or more of the corresponding implantable electrodes.

In some embodiments, the stimulation signal generator 206 generates a first stimulation signal to deliver to the first implantable electrode 202 to stimulate the first nerve and activate at least one muscle for an upper airway dilation for the patient. While not wanting to be bound by theory, it is believed that the duration of upper airway patency can follow the first stimulation cycle of the first stimulation signal, which in turn can make the patient's natural breathing rhythm follow and synchronize with the first stimulation cycle of the first stimulation signal, in other words, the entrainment of the patient's natural breathing rhythm with the first stimulation signal. For example, in the embodiment depicted in FIG. 5, the stimulation signal 512 can be the first stimulation signal. The stimulation signal cycle 513 of the first stimulation signal 512 is substantially synchronized with the respiratory cycle of the patient's respiratory waveform 502. The onset of the stimulation period 513 of the first stimulation signal 512 is substantially aligned with the onset of the inspiratory phase 503 of the patient's respiratory waveform 502.

In some embodiments, the stimulation signal generator 206 generates a second stimulation signal to deliver to the second implantable electrode 204 to stimulate the second nerve and activate at least one muscle for a caudal tracheal traction for an upper airway for the patient. While not wanting to be bound by theory, it is believed that the duration of upper airway patency can follow the second stimulation cycle of the second stimulation signal, which in turn can make the patient's natural breathing rhythm follow and synchronize with the second stimulation cycle of the second stimulation signal, in other words, the entrainment of the patient's natural breathing rhythm with the second stimulation signal. For example, in the embodiment depicted in FIG. 5, the stimulation signal 512 can be the second stimulation signal. The stimulation signal cycle 513 of the second stimulation signal 512 is substantially synchronized with the respiratory cycle of the patient's respiratory waveform 502. The onset of the stimulation period 513 of the second stimulation signal 512 is substantially aligned with the onset of the inspiratory phase 503 of the patient's respiratory waveform 502.

Figure 5B:
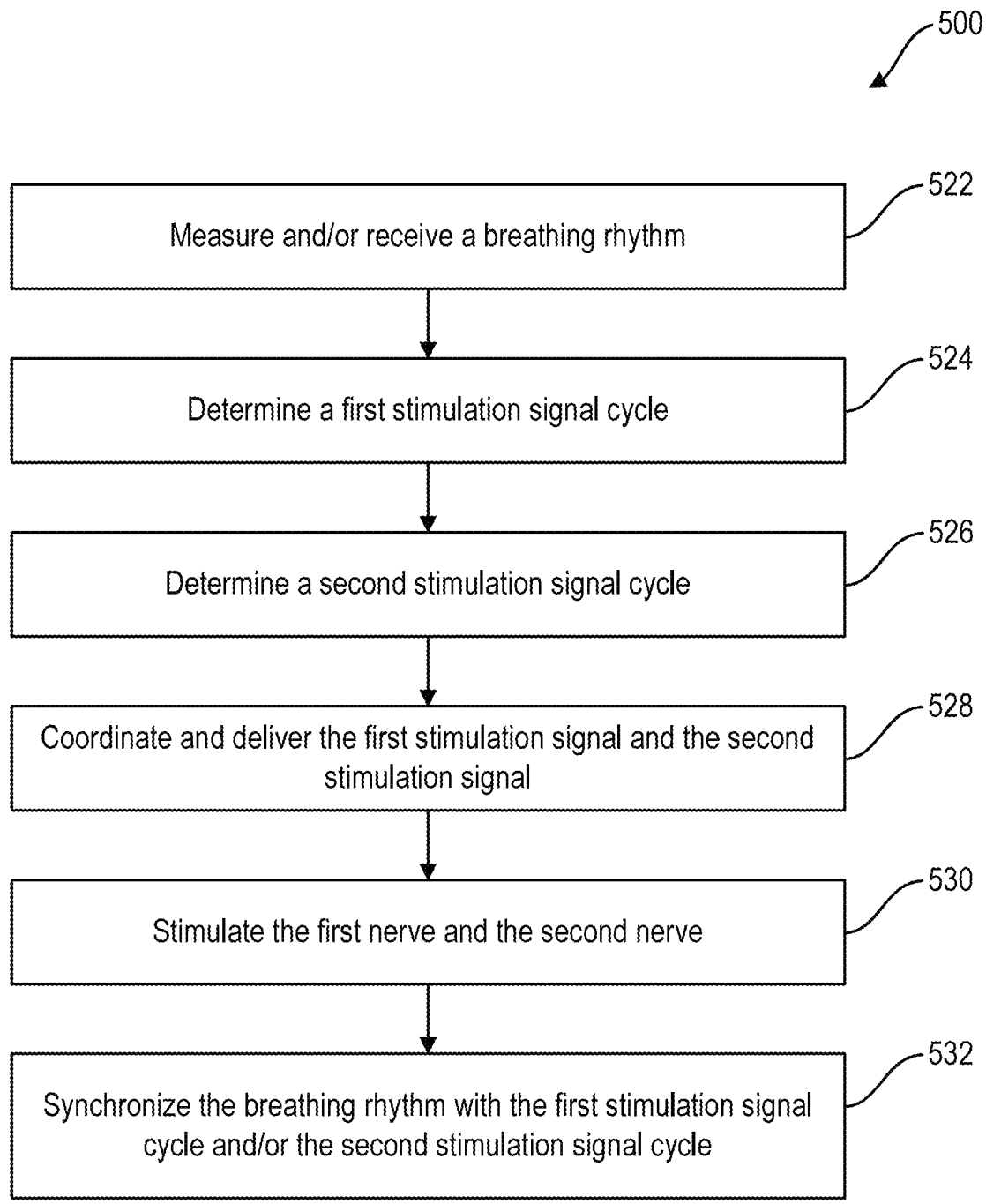
FIG. 5B is an example flow diagram of a medical method for managing obstructive sleep apnea of a patient through upper airway dual neurostimulation, in accordance with embodiments of the present disclosure.

FIG. 5B is a flow diagram of a medical method 500 for managing obstructive sleep apnea of a patient through upper airway dual neurostimulation, in accordance with embodiments of the present disclosure.

It is to be understood that any stimulation signal generators and electrodes can be used in the method. Aspects of embodiments of the method may be performed, for example, by a medical system or a controller (e.g., the medical system 200 in FIG. 2, the controller 210 in FIG. 2). One or more steps or blocks of method are optional and/or can be modified by one or more steps of other embodiments described herein. Additionally, one or more steps of other embodiments described herein may be added to the method.

According to certain embodiments, at process 522, the patient's natural breathing rhythm, such as the respiratory waveform 502 of FIG. 5A, can be measured or received. It is to be understood that the patient's natural breathing rhythm can be pre-measured or predetermined for a specific patient. In some embodiments, the controller 210 can access to the data repository 212 to obtain a historical respiratory waveform for the specific patient.

According to certain embodiments, at process 524, a first stimulation signal cycle of the first stimulation signal can be determined based at least in part on the patient's respiratory waveform. In some examples, the first stimulation signal cycle of the first stimulation signal (e.g., the stimulation signal cycle 514 of the stimulation signal 512 of FIG. 5A) can be controlled or adjusted to have a duration substantially the same as the duration of a respiratory cycle of the historical respiratory waveform 502.

According to certain embodiments, at process 526, a second stimulation signal cycle of the second stimulation signal can be determined based at least in part on the patient's respiratory waveform and/or the first stimulation signal. In some examples, the second stimulation signal cycle of the second stimulation signal (e.g., the stimulation signal cycle 514 of the stimulation signal 512 of FIG. 5A) can be controlled or adjusted to have a duration substantially the same as the duration of a respiratory cycle of the historical respiratory waveform 502.

According to certain embodiments, at process 528, the first stimulation signal and the second stimulation signal can be coordinated to be delivered proximate to a first nerve and a second nerve, respectively.

According to certain embodiments, at process 530, the first stimulation signal is delivered to stimulate the first nerve, and the second stimulation signal is delivered to stimulate the second nerve. In some embodiments, the first stimulation signal is delivered to stimulate a first hypoglossal nerve to activate tongue protrusors (e.g., genioglossus), and avoid stimulating certain nerve branches which may activate suprahyoid muscles (e.g., geniohyoid) and avoid stimulating certain nerve branches which may activate retractor muscles of the tongue muscles (e.g., styloglossus and/or hyoglossus). In some embodiments, the second stimulation signal is delivered to stimulate the first ansa cervicalis nerve to activate infrahyoid muscles (e.g., sternothyroid and/or sternohyoid), and avoid stimulating certain nerve branches which may activate suprahyoid muscles (e.g., geniohyoid). In some embodiments, the second implantable electrode can be implanted to deliver the second stimulation signal to stimulate certain nerve branch(es) of the ansa cervicalis and activate sternothyroid and sternohyoid muscles simultaneously, while avoiding stimulating certain nerve branches which may activate suprahyoid muscles (e.g., geniohyoid).

According to certain embodiments, at process 532, the patient's breathing rhythm can be synchronized with the first stimulation signal cycle and/or the second stimulation signal cycle to achieve the entrainment of the patient's natural breathing rhythm with the dual neurostimulation by using the coordinated first and second stimulation signals.

Figure 6A:
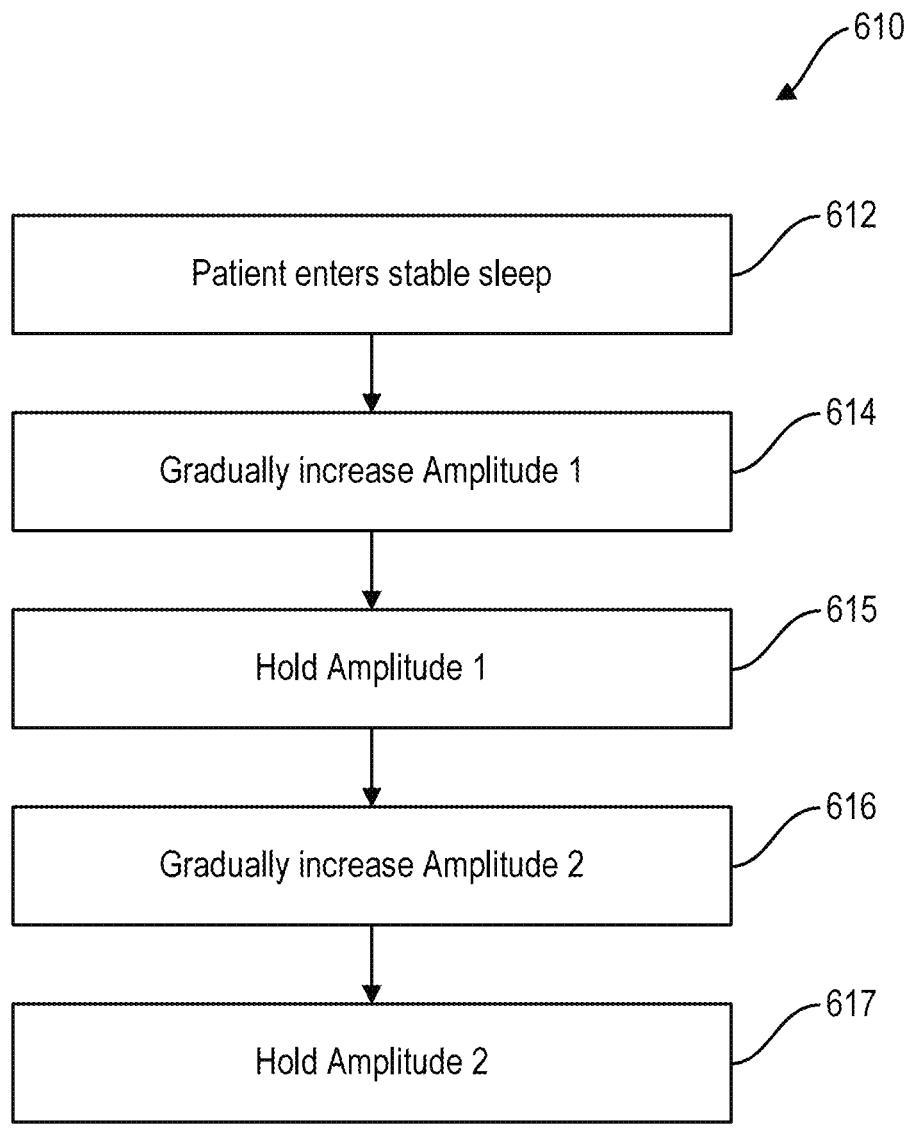
FIGS. 6A-C are example flow diagrams illustrating titration methods, in accordance with some embodiments of the present disclosure.
Figure 6B:
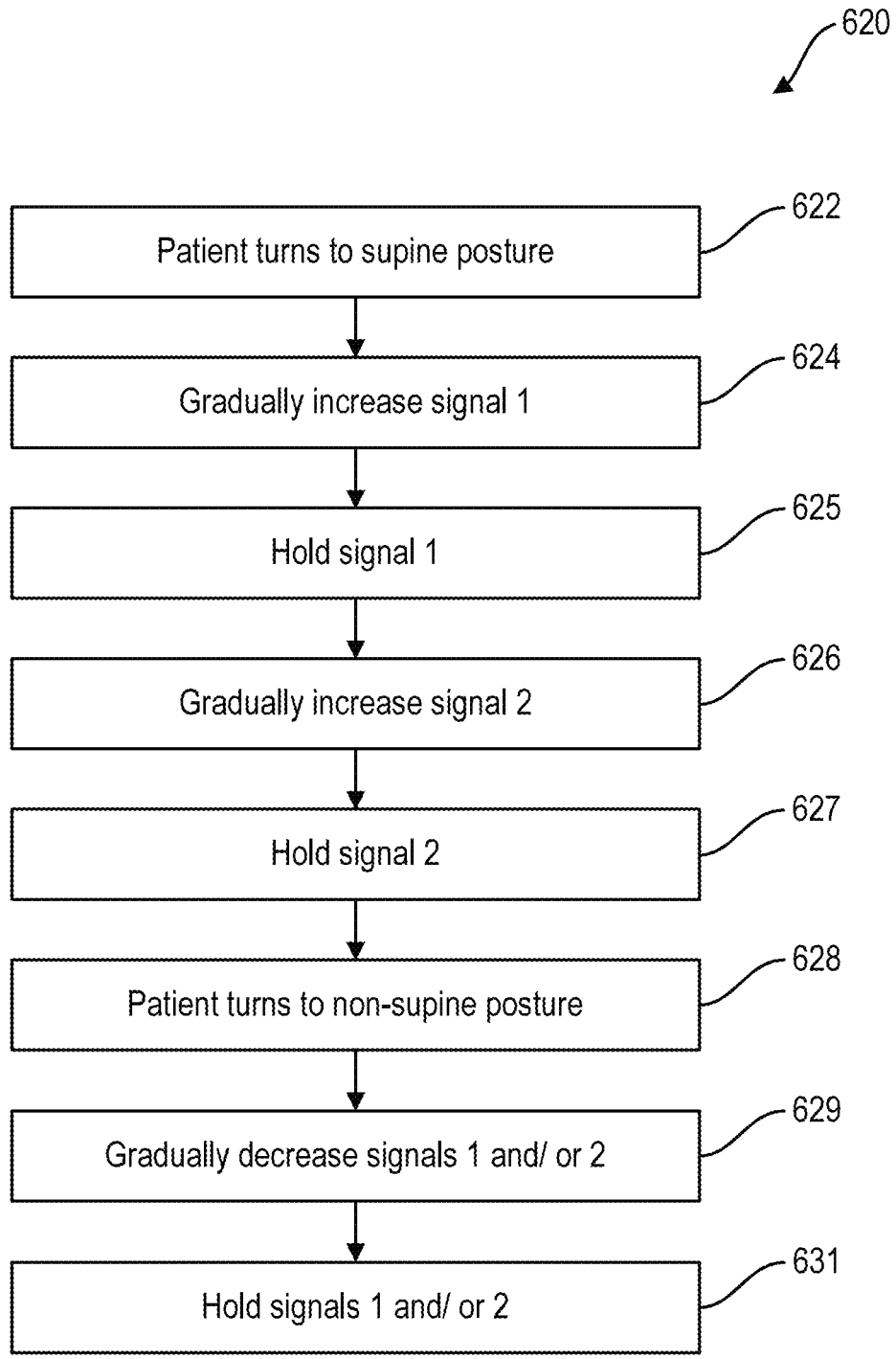
Figure 6C:
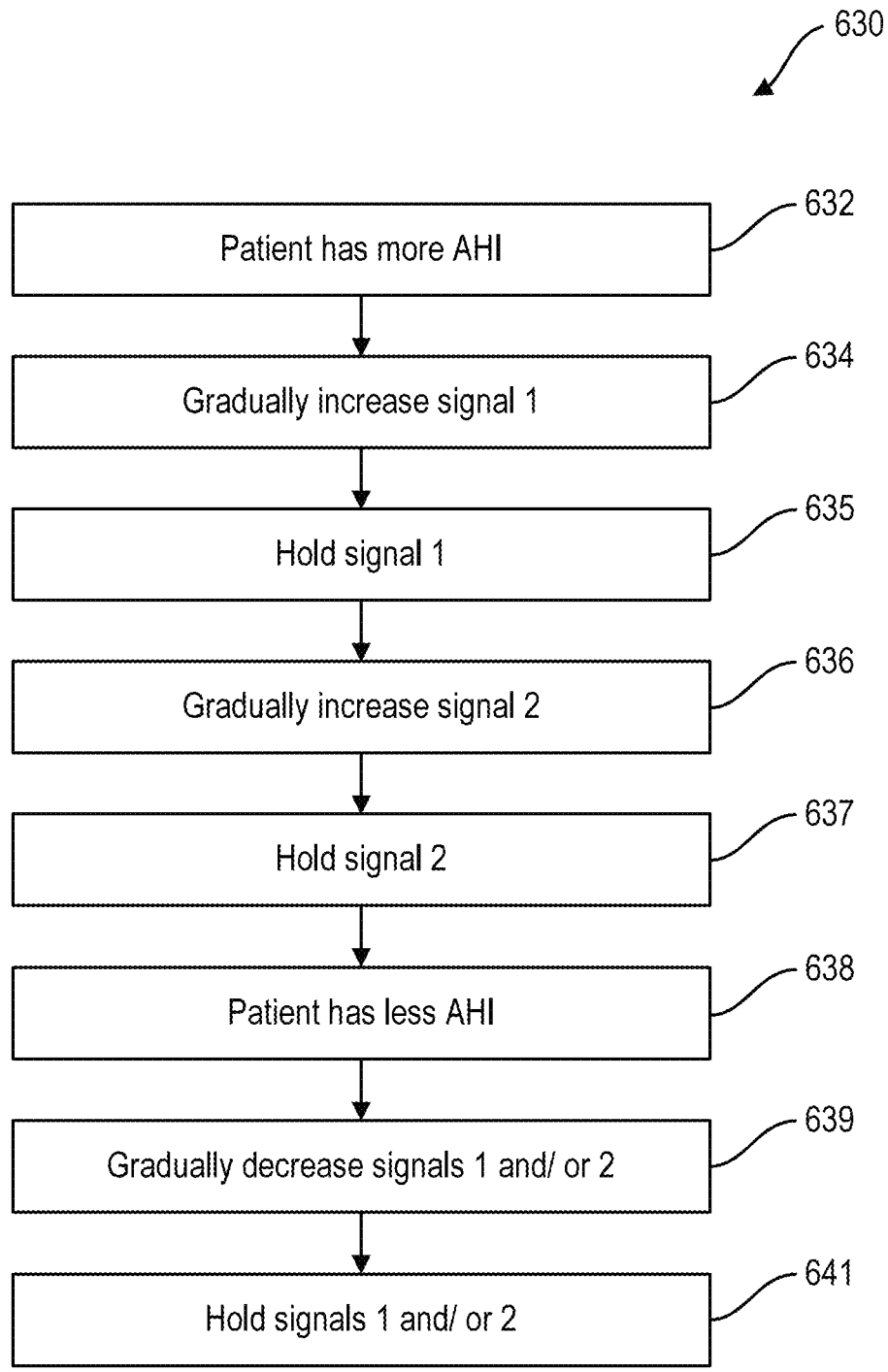

FIGS. 6A-C are flow diagrams illustrating various example titration methods to develop stimulation therapies or settings for managing obstructive sleep apnea (OSA) for a person, in accordance with some embodiments of the present disclosure. In some embodiments, the obtained stimulation therapies or settings can be provided to the controller 210 or the stimulation signal generator 206 as programmable settings to modulate one or more stimulation signals.

In a first titration method 610, as illustrated in FIG. 6A, when a patient is detected entering a stable sleep at block 612, the first stimulation signal is gradually increased from a lower level to a higher level at block 614 and held at the higher level for a first period at block 615. The lower level can be, for example, a lower pulse amplitude, a lower pulse width, a lower duty cycle, a lower pulse frequency, and the like. The higher level can be, for example, a higher pulse width, a higher pulse amplitude, a higher duty cycle, a higher pulse frequency, and the like. In some embodiments, the lower level can be a functional or sensational threshold level at which the patient starts to feel the stimulation. For example, the lower level can be a level at which the patient's tongue starts protruding through stimulation of the first stimulation signal at the functional (bulk movement of the tongue or hyoid and thyroid complex) or sensational (the lowest level of stimulation with patient perception of stimulation) threshold level. In some embodiments, the higher level can be, for example, a saturation level at which the patient's AHI starts to be stabilized. With the first stimulation signal being held at the saturation level, the second stimulation signal can be gradually increased from a lower level to a higher level at block 616 and held at the higher level for a second period at block 617. It is to be understood that the lower/higher level of the first stimulation signal can be different from the lower/higher level of the second stimulation signal, which may depend on the characteristics of the respective first and second nerves to be stimulated.

In a second titration method 620, as illustrated in FIG. 6B, when a patient is detected turning to a supine posture at block 622, the first stimulation signal is gradually increased from a lower level to a higher level at block 624 and held at the higher level for a first period at block 625. The lower level can be, for example, a lower pulse amplitude, a lower pulse width, a lower duty cycle, and the like. The higher level can be, for example, a higher pulse width, a higher pulse amplitude, a higher duty cycle, and the like. In some embodiments, the lower level can be a functional or sensational threshold level at which the patient starts to feel the stimulation. For example, the lower level can be a level at which the patient's tongue starts protruding through stimulation of the first stimulation signal at the functional or sensational threshold level. In some embodiments, the higher level can be, for example, a saturation level at which the patient's AHI starts to be stabilized. With the first stimulation signal being held at the saturation level, the second stimulation signal can be gradually increased from a lower level to a higher level at block 626 and held at the higher level for a second period at block 627. It is to be understood that the respective lower levels and higher levels for the first and second stimulation signals may be different. When the patient is detected turning to a non-supine posture at block 628, the first stimulation signal and/or the second stimulation signal can be gradually decreased from the respective higher levels to respective second lower levels at block 629 and held at the respective second lower levels for a third period at block 631. The second lower levels may be the same as or different from the previous lower levels.

In a third titration method 630, as illustrated in FIG. 6C, when a patient is detected having an increased AHI at block 632, the first stimulation signal is gradually increased from a lower level to a higher level at block 634 and held at the higher level for a first period at block 635. The lower level can be, for example, a lower pulse amplitude, a lower pulse width, a lower duty cycle, and the like. The higher level can be, for example, a higher pulse width, a higher pulse amplitude, a higher duty cycle, and the like. In some embodiments, the lower level can be a functional or sensational threshold level at which the patient starts to feel the stimulation. For example, the lower level can be a level at which the patient's tongue starts protruding through stimulation of the first stimulation signal at the functional or sensational threshold level. In some embodiments, the higher level can be, for example, a saturation level at which the patient's AHI starts to be stabilized. With the first stimulation signal being held at the saturation level, the second stimulation signal can be gradually increased from a lower level to a higher level at block 636 and held at the higher level for a second period at block 637. When a patient is detected having the AHI decreased to a predetermined range (e.g., 5 or less) at block 638, the first stimulation signal and/or the second stimulation signal can be gradually decreased from the respective higher levels to respective second lower levels at block 639 and held at the respective second levels for a fourth period at block 641.

According to certain embodiments, in any of the titration methods (e.g., the first, second or third titration method 610, 620, 630), the patient's AHI can be monitored by the sensors 214 of FIG. 2 in real time to adjust one or more first parameters (e.g., the first amplitude, the first period, and the like) of the first stimulation signal and one or more second parameters (e.g., the second amplitude, the second period, and the like) of the second stimulation signal to optimize the method and obtain an optimized therapy for managing obstructive sleep apnea (OSA) for the patient.

Figure 7A:
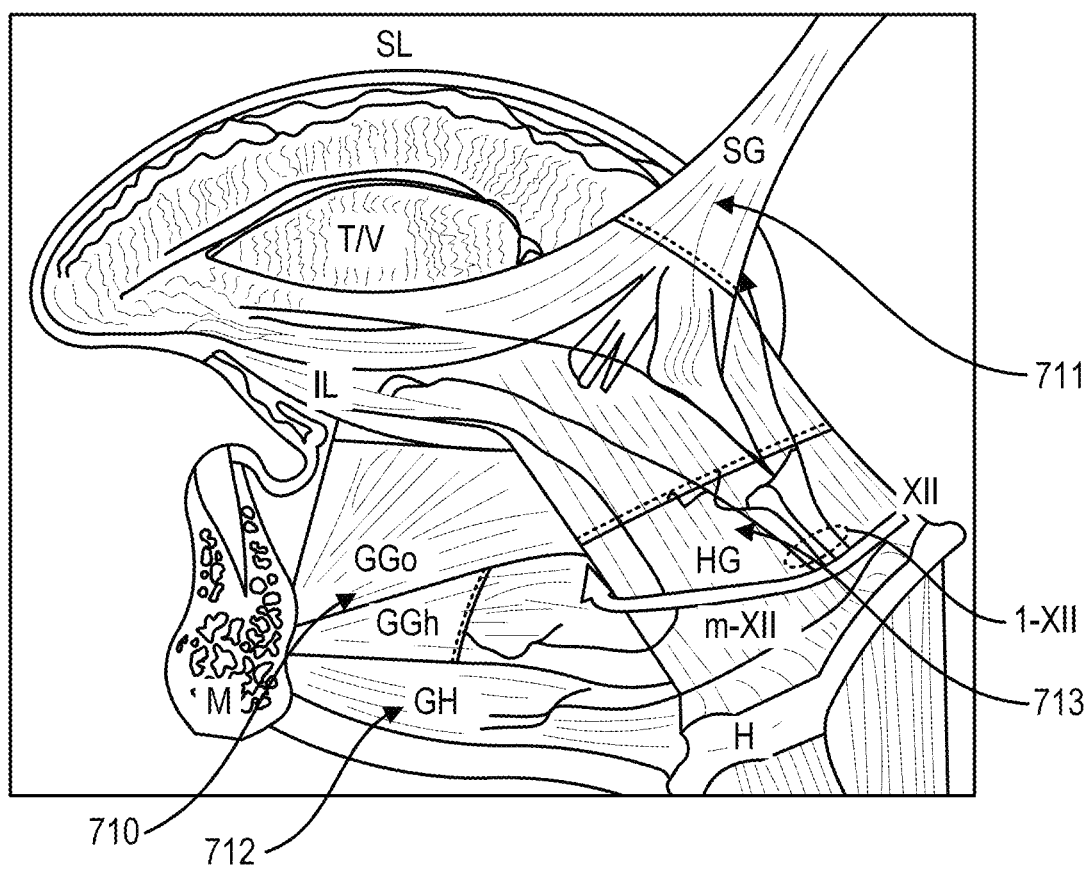
FIG. 7A illustrates a schematic diagram representing patient anatomy and example target muscle location(s) for hypoglossal nerve stimulation, in accordance with embodiments of the present disclosure.

FIG. 7A illustrates a schematic diagram representing patient anatomy and target muscle location(s) for hypoglossal nerve stimulation, in accordance with embodiments of the present disclosure. In some embodiments, one or more first implantable electrodes deliver a first stimulation signal proximate to a first hypoglossal nerve to activate tongue protrusors (e.g., genioglossus 710). In some embodiments, an implantable electrode can be positioned to deliver the first stimulation signal proximate to one or more medial branches of the hypoglossal nerve (m-XII) to stimulate the one or more medial branches and activate one or more protrusion muscles of the tongue muscles including genioglossus 710. In some embodiments, the one or more first implantable electrodes deliver the first stimulation signal to avoid activating suprahyoid muscles (e.g., geniohyoid 712). In some embodiments, the one or more first implantable electrodes are positioned to avoid activating one or more retractor muscles of the tongue muscles including styloglossus 711 and hyoglossus 713.

Figure 7B:
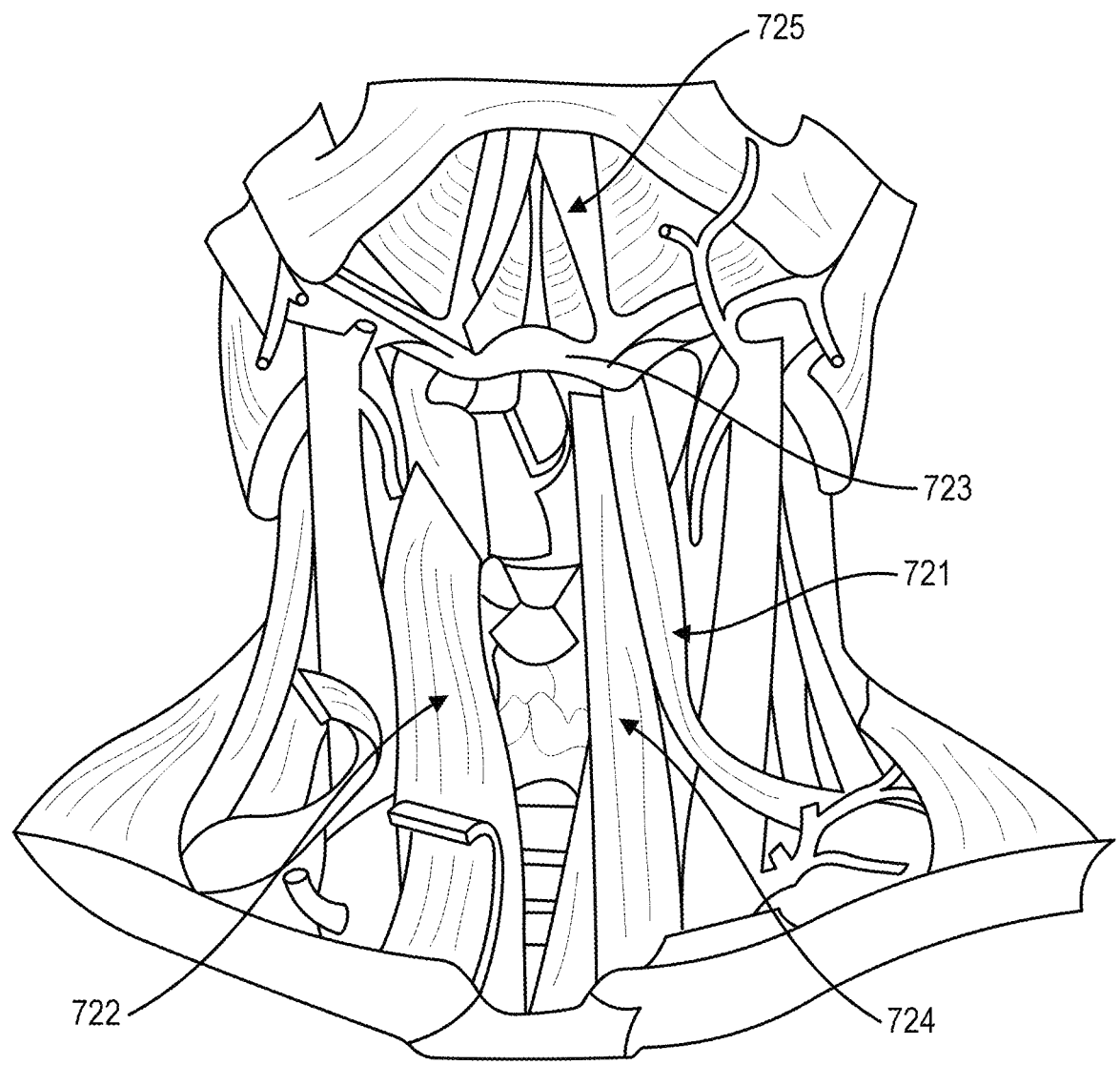
FIG. 7B illustrates a schematic diagram representing patient anatomy and example target muscle location(s) for ansa cervicalis stimulation, in accordance with embodiments of the present disclosure.

FIG. 7B illustrates a schematic diagram representing patient anatomy and target muscle location(s) for ansa cervicalis stimulation, in accordance with embodiments of the present disclosure. In some embodiments, one or more second implantable electrodes deliver a second stimulation signal proximate to a first ansa cervicalis nerve to stimulate the first ansa cervicalis nerve to activate infrahyoid muscles including sternothyroid 722, sternohyoid 724, and omohyoid 721, which are below the hyoid 723. In some embodiments, the second implantable electrode can be implanted to deliver the second stimulation signal to stimulate certain nerve branch(es) of the ansa cervicalis and activate sternothyroid 722 and sternohyoid 724 simultaneously. In some embodiments, the one or more first implantable electrodes and second implantable electrodes are positioned to deliver the first and second stimulation signals to avoid activating suprahyoid muscles 725 (see also, e.g., geniohyoid 712 of FIG. 7A) which are above the hyoid 723. Activating the suprahyoid muscles 725 may counteract the effects of activating the infrahyoid muscles including sternothyroid 722 and sternohyoid 724 and it can be desirable to avoid activating the suprahyoid muscles 725 by properly positioning the first implantable electrodes.

It is to be understood that when the first stimulation signal is used alone (i.e., not working with the second stimulation signal at the same time) to activate tongue protrusors, it may be acceptable for the first stimulation signal to also activate the suprahyoid muscles (e.g., geniohyoid). When an upper airway dual neurostimulation including both hypoglossal nerve stimulation and ansa cervicalis stimulation is implemented as described herein, in some embodiments, it is desirable to avoid activating the suprahyoid muscles (e.g., geniohyoid) since such an activating may counteract the effects of the ansa cervicalis stimulation.

Figure 7C:
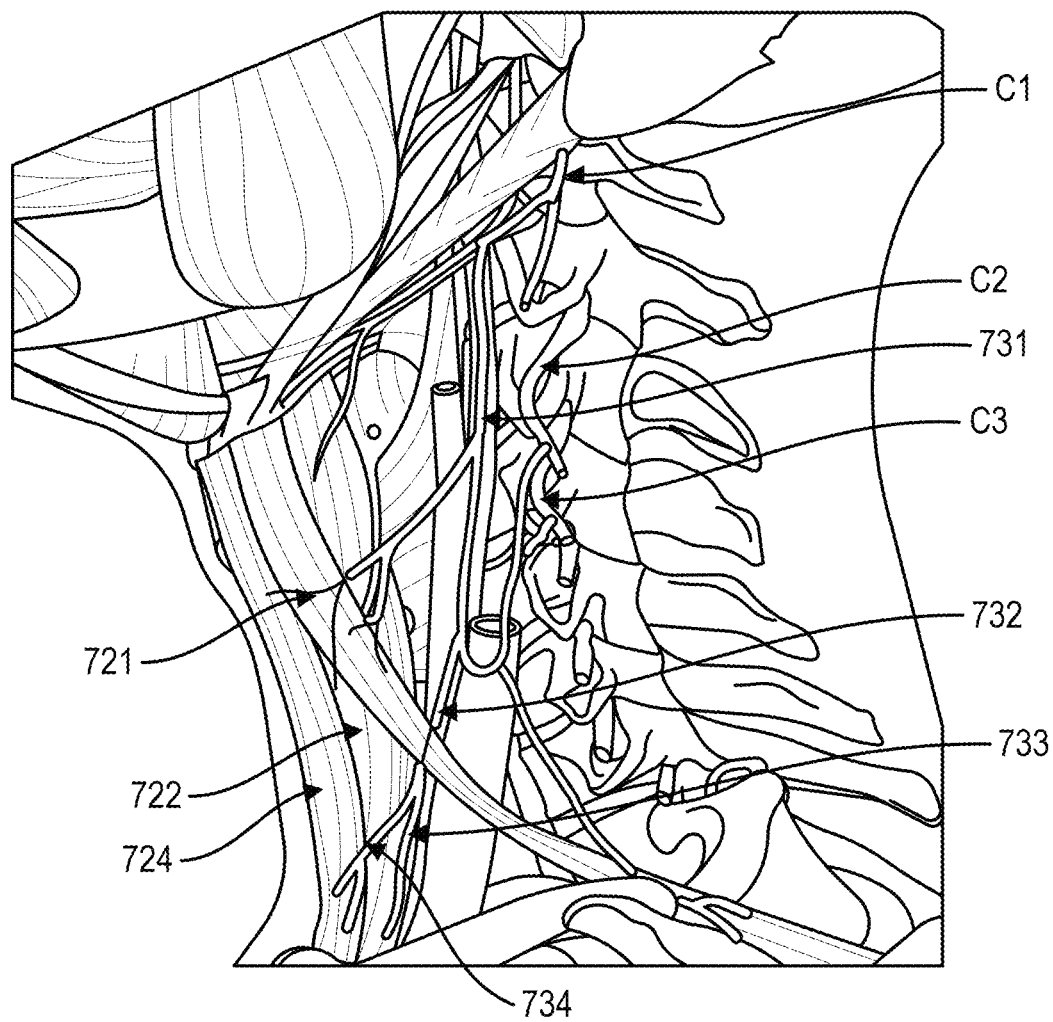
FIG. 7C illustrates a schematic diagram representing patient anatomy and example target nerve/muscle location(s) for an upper airway dual neurostimulation including hypoglossal nerve stimulation and ansa cervicalis stimulation, in accordance with embodiments of the present disclosure.

FIG. 7C illustrates a schematic diagram representing patient anatomy and target nerve/muscle location(s) for an upper airway dual neurostimulation including hypoglossal nerve stimulation and ansa cervicalis stimulation, in accordance with embodiments of the present disclosure. In some embodiments, the target or desired nerve/muscle location(s) for the upper airway dual neurostimulation can include, for example, one or more infrahyoid muscles (e.g., sternothyroid 722, sternohyoid 724, and omohyoid 721). FIG. 7C further illustrates the relevant locations such as a common trunk 731 to omohyoid, sternothyroid and sternohyoid, a common trunk 732 to sternothyroid and sternohyoid, a never trunk 733 to sternothyroid, a never trunk 734 to sternohyoid, a first cervical (C1) spinal nerve, a second cervical (C2) spinal nerve, and a third cervical (C3) spinal nerve. In some embodiments, the upper airway dual neurostimulation can avoid stimulating or activating the nerve/muscle location(s) including, for example, styloglossus, hyoglossus, and geniohyoid.

Figure 7D:
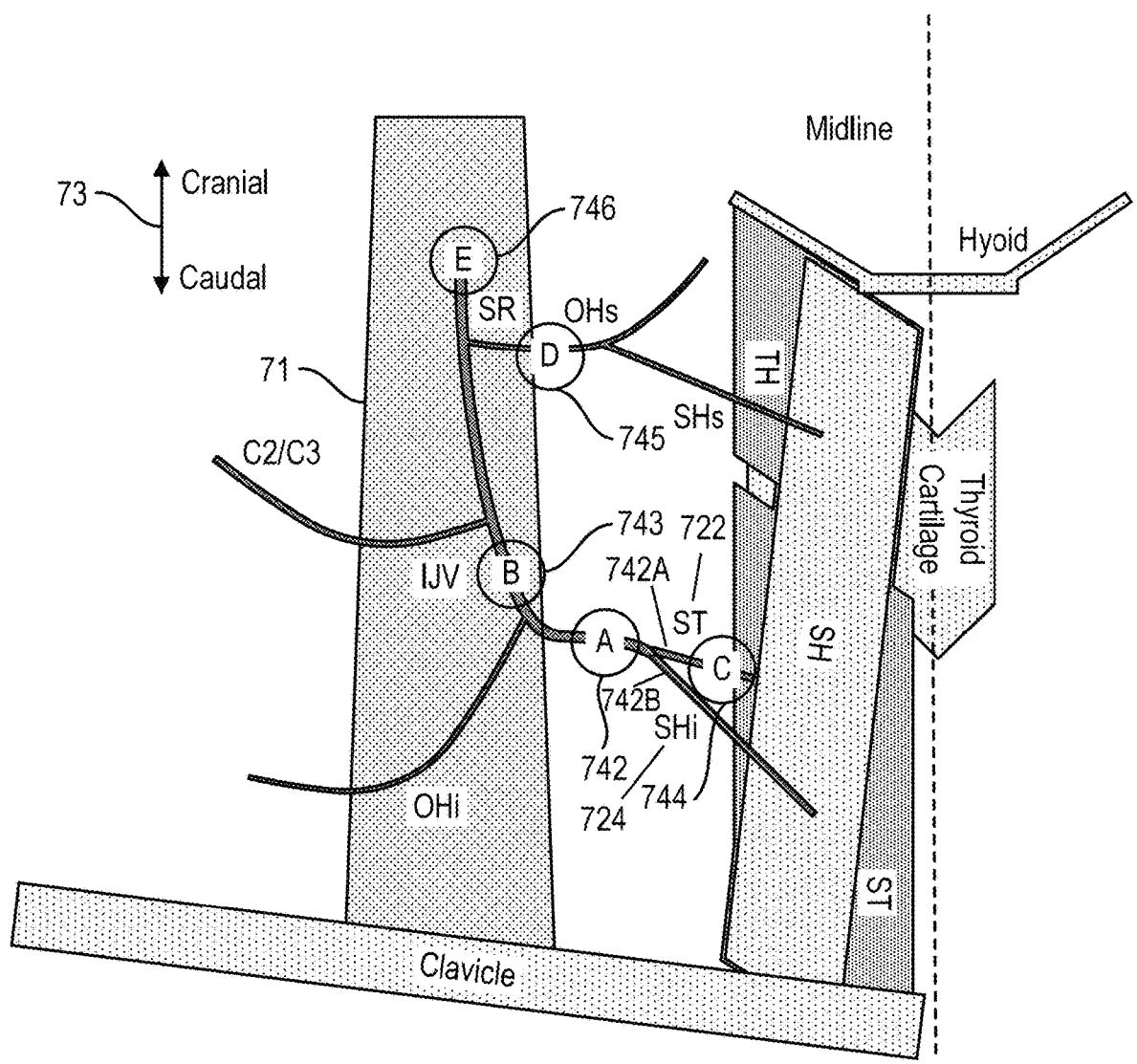
FIG. 7D illustrates a schematic diagram representing patient anatomy and example target nerve/muscle location(s) for ansa cervicalis stimulation in an upper airway dual neurostimulation, in accordance with embodiments of the present disclosure.

FIG. 7D illustrates a schematic diagram representing patient anatomy and target nerve/muscle location(s) for ansa cervicalis stimulation in an upper airway dual neurostimulation, in accordance with embodiments of the present disclosure. FIG. 7D illustrates the locations for various ansa cervicalis nerves including the superior root (SR), the omohyoid superior (OHs), the sternohyoid superior (SHs), the sternothyroid (ST), the sternohyoid inferior (SHi), and the omohyoid inferior (OHi). FIG. 7D also illustrates the locations for various muscles including the sternohyoid muscle (SH), the sternothyroid muscle (ST), and the thyrohyoid muscle (TH). The internal jugular vein (IJV) 71 and the cranial/caudal direction 73 are also shown. The target stimulation locations can include one or more of location A 742, location B 743, location C 744, location D 745, and location E 746. In some embodiments, a single implanted stimulation lead can be disposed at or proximate to one of locations A to E 742, 743, 744, 745 and 746. For example, a single implanted stimulation lead can be located at or proximate to location A 742 to deliver a stimulation signal. In some embodiments, the stimulation signal can be delivered at or proximate to location A 742 to stimulate two or more relevant nerve branch(es) of the ansa cervicalis simultaneously, for example, to activate sternothyroid (ST) 722 and sternohyoid (SHi) 724 simultaneously. In certain embodiments, a stimulation lead can be disposed (e.g., delivered to) at or proximate to a nerve segment connecting to two or more nerve branches. For example, the stimulation lead can be disposed at or proximate to the location 742 that is a nerve segment connecting to branch 742A and branch 742B. In some embodiments, the stimulation signal can be delivered at or proximate to a nerve segment connecting to two or more nerve branches. In some embodiments, a first implanted stimulation lead can be located at or proximate to one of location A 742, location B 743 and location C 744, and a second implanted stimulation lead can be located at or proximate to location E 746 or location D 745. In some embodiments, location A 742 and location B 743 can be superior to location C 744 due to the relatively closer distance to the internal jugular vein (IJV) 741 and/or the relatively larger nerve size (as indicated by the respective line thicknesses). In some embodiments, a first implanted stimulation lead can be located at or proximate to location A 742 or B 743, and a second implanted stimulation lead can be located at or proximate to location E 746.

In some embodiments, the controller 210 is configured to modulate the second stimulation signal between a lower stimulation level and a higher stimulation level to activate the one or more infrahyoid muscles within a strain range between a first strain value and a second strain value. In some embodiments, the strain can be measured by a displacement of the hyoid bone. The displacement can be an absolute displacement in a range, for example, from about 5 mm to about 20 mm, which can correspond to the first strain value and the second strain value, respectively. It is to be understood that the displacement or strain can be represented by a relative value, for example, a percentage. A lower level of the second stimulation signal corresponds to the first strain value, and a higher level of the second stimulation signal corresponds to the second strain value. An optimum stimulation level can be determined between the lower stimulation level and the higher stimulation level to provide an optimum strain to provide a caudal tracheal traction for an upper airway of the patient. The optimum strain level can prevent possible upper airway collapse or flow limitation. In some embodiments, the optimum stimulation level can be determined by using the measured strain levels (e.g., as indicated by the displacement of the hyoid bone) as feedback. For example, a series of stimulation levels can be applied, and the corresponding the displacements of the hyoid bone can be measured to determine the optimum stimulation level.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

According to some embodiments of the present disclosure, a system for managing obstructive sleep apnea for a person is provided. The system includes a first implantable electrode configured to deliver a first stimulation signal proximate to a first nerve of the person to stimulate the first nerve and activate at least one first muscle for an upper airway dilation of the person; a second implantable electrode configured to deliver a second stimulation signal proximate to a second nerve to stimulate the second nerve and activate at least one second muscle for a caudal tracheal traction for an upper airway of the person; and a stimulation signal generator configured to deliver the first stimulation signal to the first implantable electrode, and deliver the second stimulation signal to the second implantable electrode, the first stimulation signal having a series of first stimulation cycles each including a first stimulation period and a first non-stimulation period, the second stimulation signal having a series of second stimulation cycles each including a second stimulation period and a second non-stimulation period, the delivery of the first stimulation signal being coordinated with the delivery of the second stimulation signal. The second stimulation signal is modulated to activate the at least one second muscle within a strain range between a first strain value and a second strain value, wherein a first stimulation level of the second stimulation signal corresponds to the first strain value, and a second stimulation level of the second stimulation signal corresponds to the second strain value.

In certain embodiments, the system further includes a controller functionally connected to the stimulation signal generator to control operation of the stimulation signal generator.

In certain embodiments, the controller is configured further to control one or more stimulation parameters for the stimulation signal generator.

In certain embodiments, the one or more stimulation parameters include one or more of an amplitude, a frequency, a pulse width, a rate of amplitude change, and a duty cycle.

In certain embodiments, the first implantable electrode is configured to deliver the first stimulation signal proximate to a hypoglossal nerve to stimulate the hypoglossal nerve and activate at least one tongue muscle.

In certain embodiments, the first implantable electrode is positioned to deliver the first stimulation signal proximate to one or more medial branches of the hypoglossal nerve (m-XII) to stimulate the one or more medial branches and activate one or more protrusion muscles of the at least one tongue muscle including genioglossus.

In certain embodiments, the second implantable electrode is configured to deliver the second stimulation signal proximate to an ansa cervicalis nerve to stimulate the ansa cervicalis nerve and activate one or more infrahyoid muscles. In some embodiments, the second stimulation signal can activate sternothyroid and sternohyoid simultaneously.

In certain embodiments, the controller is configured to modulate the second stimulation signal to activate the one or more infrahyoid muscles within the strain range between the first strain value and the second strain value, wherein a first amplitude level of the second stimulation signal corresponds to the first strain value, and a second amplitude level of the second stimulation signal corresponds to the second strain value.

In certain embodiments, the controller is configured to control the operation of the stimulation signal generator in a first mode, wherein the stimulation signal generator is configured to synchronize the first stimulation periods and the first non-stimulation periods of the first stimulation signal with the second stimulation periods and the second non-stimulation periods of the second stimulation signal, respectively.

In certain embodiments, the controller is configured to control the operation of the stimulation signal generator in a second mode, wherein a first duration of the first stimulation period is greater than a second duration of the second stimulation period.

In certain embodiments, in the second mode, the first duration of the first stimulation period is two or more times greater than the second duration of the second stimulation period.

In certain embodiments, the stimulation signal generator is configured to coordinate the delivery of the first stimulation signal and the delivery of the second stimulation signal based at least in part on a historical respiratory waveform.

In certain embodiments, the stimulation signal generator comprises an internal timer to provide timing to coordinate the series of first stimulation cycles and the series of second stimulation cycles, independent of a respiratory status of the person.

In certain embodiments, the system further includes one or more sensors to detect one or more physiological parameters including an apnea-hypopnea index (AHI), a posture change, a sleep stage, and a time of day.

In certain embodiments, the controller is configured to control one or more stimulation parameters of the stimulation signal generator based at least in part on the one or more physiological parameters.

In certain embodiments, the controller further comprises a patient controller to control operation of the stimulation signal generator, including to turn on or turn off the stimulation signal generator.

In certain embodiments, the system further includes a third implantable electrode configured to deliver a third stimulation signal proximate to a third nerve to stimulate the third nerve.

According to certain embodiments of the present disclosure, a method for managing obstructive sleep apnea for a person is provided. The method includes providing a first implantable electrode configured to deliver a first stimulation signal proximate to a first nerve to stimulate the first nerve and activate at least one first muscle for upper airway dilation; providing a second implantable electrode configured to deliver a second stimulation signal proximate to a second nerve to stimulate the second nerve and activate at least one second muscle for a caudal tracheal traction for an upper airway of the person; modulating the second stimulation signal to activate the at least one second muscle within a strain range between a first strain value and a second strain value, wherein a first stimulation level of the second stimulation signal corresponds to the first strain value, and a second stimulation level of the second stimulation signal corresponds to the second strain value; delivering the first stimulation signal to the first implantable electrode; and delivering the second stimulation signal to the second implantable electrode, wherein the first stimulation signal and the second stimulation signal are coordinated, and wherein the first stimulation signal has a series of first stimulation cycles each including a first stimulation period and a first non-stimulation period, the second stimulation signal has a series of second stimulation cycles each including a second stimulation period and a second non-stimulation period.

In certain embodiments, the method further includes controlling one or more first stimulation parameters for the first stimulation signal; and controlling one or more second stimulation parameters for the second stimulation signal.

In certain embodiments, the one or more first stimulation parameters and the one or more second stimulation parameters each include one or more of an amplitude, a frequency, a pulse width, a rate of amplitude change, and a duty cycle.

In certain embodiments, the first implantable electrode is configured to deliver the first stimulation signal proximate to a hypoglossal nerve to stimulate the hypoglossal nerve and activate at least one tongue muscle.

In certain embodiments, delivering the first stimulation signal further includes delivering the first stimulation signal proximate to one or more medial branches of the hypoglossal nerve (m-XII) to stimulate the one or more medial branches and activate one or more protrusion muscles of the at least one tongue muscle including genioglossus.

In certain embodiments, the second implantable electrode is configured to deliver a second stimulation signal proximate to an ansa cervicalis nerve to stimulate the ansa cervicalis nerve and activate one or more infrahyoid muscles including sternothyroid and sternohyoid. In some embodiments, the second stimulation signal can activate sternothyroid and sternohyoid simultaneously.

In certain embodiments, modulating the second stimulation signal to activate the at least one second muscle further comprises modulating the second stimulation signal to activate the one or more infrahyoid muscles within the strain range between the first strain value and the second strain value, wherein a first amplitude level of the second stimulation signal corresponds to the first strain value, and a second amplitude level of the second stimulation signal corresponds to the second strain value.

In certain embodiments, the method further includes controlling operation of a stimulation signal generator in a first mode, wherein the stimulation signal generator is configured to synchronize the first stimulation periods and the first non-stimulation periods of the first stimulation signal with the second stimulation periods and the second non-stimulation periods of the second stimulation signal, respectively.

In certain embodiments, the method further includes controlling operation of a stimulation signal generator in a second mode, wherein a first duration of the first stimulation period is two or more times greater than a second duration of the second stimulation period.

In certain embodiments, the method further includes coordinating the delivery of the first stimulation signal and the delivery of the second stimulation signal based at least in part on a historical respiratory waveform of the person.

In certain embodiments, the method further includes synchronizing the series of first stimulation cycles of the first stimulation signal with a current respiratory waveform of the person.

In certain embodiments, the method further includes synchronizing the series of second stimulation cycles of the second stimulation signal with a current respiratory waveform of the person.

In certain embodiments, the method further includes providing timing to coordinate the series of first stimulation cycles and the series of second stimulation cycles by using an internal timer, independent of a respiratory status of the person.

In certain embodiments, the method further includes detecting one or more physiological parameters including an apnea-hypopnea index (AHI), a posture change, a sleep stage, and a time of day.

In certain embodiments, the method further includes controlling one or more stimulation parameters of the stimulation signal generator based at least in part on the one or more physiological parameters.

Various modifications and additions can be made to the exemplary embodiments discussed without departing from the scope of the present disclosure. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A system for managing obstructive sleep apnea for a person, the system comprising:
    a first implantable electrode configured to deliver a first stimulation signal proximate to a first nerve of the person to stimulate the first nerve and activate at least one first muscle for an upper airway dilation of the person;
    a second implantable electrode configured to deliver a second stimulation signal proximate to a second nerve to stimulate the second nerve and activate at least one second muscle for a caudal tracheal traction for an upper airway of the person; and
    a stimulation signal generator configured to deliver the first stimulation signal to the first implantable electrode, and deliver the second stimulation signal to the second implantable electrode, the first stimulation signal having a series of first stimulation cycles each including a first stimulation period and a first non-stimulation period, the second stimulation signal having a series of second stimulation cycles each including a second stimulation period and a second non-stimulation period, the delivery of the first stimulation signal being coordinated with the delivery of the second stimulation signal,
    wherein the second stimulation signal is modulated to activate the at least one second muscle within a strain range between a first strain value and a second strain value, wherein a first stimulation level of the second stimulation signal corresponds to the first strain value, and a second stimulation level of the second stimulation signal corresponds to the second strain value.

2. The system of claim 1, further comprising a controller functionally connected to the stimulation signal generator to control operation of the stimulation signal generator.

3. The system of claim 2, wherein the controller is configured further to control one or more stimulation parameters for the stimulation signal generator.

4. The system of claim 3, wherein the one or more stimulation parameters include one or more of an amplitude, a frequency, a pulse width, a rate of amplitude change, and a duty cycle.

5. The system of claim 1, wherein the first implantable electrode is configured to deliver the first stimulation signal proximate to a hypoglossal nerve to stimulate the hypoglossal nerve and activate at least one tongue muscle.

6. The system of claim 5, wherein the first implantable electrode is positioned to deliver the first stimulation signal proximate to one or more medial branches of the hypoglossal nerve (m-XII) to stimulate the one or more medial branches and activate one or more protrusion muscles of the at least one tongue muscle including genioglossus.

7. The system of claim 1, wherein:
    the second implantable electrode is configured to deliver the second stimulation signal proximate to an ansa cervicalis nerve to stimulate the ansa cervicalis nerve and activate one or more infrahyoid muscles.

8. The system of claim 7, wherein the second stimulation signal is further configured to activate sternothyroid and sternohyoid simultaneously.

9. The system of claim 7, wherein the controller is configured to modulate the second stimulation signal to activate the one or more infrahyoid muscles within the strain range between the first strain value and the second strain value, wherein a first amplitude level of the second stimulation signal corresponds to the first strain value, and a second amplitude level of the second stimulation signal corresponds to the second strain value.

10. The system of claim 2, wherein the controller is configured to control the operation of the stimulation signal generator in a first mode, wherein the stimulation signal generator is configured to synchronize the first stimulation periods and the first non-stimulation periods of the first stimulation signal with the second stimulation periods and the second non-stimulation periods of the second stimulation signal, respectively.

11. The system of claim 2, wherein the controller is configured to control the operation of the stimulation signal generator in a second mode, wherein a first duration of the first stimulation period is greater than a second duration of the second stimulation period.

12. The system of claim 11, wherein in the second mode, the first duration of the first stimulation period is two or more times greater than the second duration of the second stimulation period.

13. The system of claim 1, wherein the stimulation signal generator is configured to coordinate the delivery of the first stimulation signal and the delivery of the second stimulation signal based at least in part on a historical respiratory waveform.

14. The system of claim 1, wherein the stimulation signal generator comprises an internal timer to provide timing to coordinate the series of first stimulation cycles and the series of second stimulation cycles, independent of a respiratory status of the person.

15. The system of claim 1, further comprising one or more sensors to detect one or more physiological parameters including an apnea-hypopnea index (AHI), a posture change, a sleep stage, and a time of day.

16. The system of claim 15, wherein the controller is configured to control one or more stimulation parameters of the stimulation signal generator based at least in part on the one or more physiological parameters.

17. The system of claim 2, wherein the controller further comprises a patient controller to control operation of the stimulation signal generator, including to turn on or turn off the stimulation signal generator.

18. The system of claim 1, further comprising a third implantable electrode configured to deliver a third stimulation signal proximate to a third nerve to stimulate the third nerve.

19. A method for managing obstructive sleep apnea for a person, the method comprising:
providing a first implantable electrode configured to deliver a first stimulation signal proximate to a first nerve to stimulate the first nerve and activate at least one first muscle for upper airway dilation;
providing a second implantable electrode configured to deliver a second stimulation signal proximate to a second nerve to stimulate the second nerve and activate at least one second muscle for a caudal tracheal traction for an upper airway of the person;
modulating the second stimulation signal to activate the at least one second muscle within a strain range between a first strain value and a second strain value, wherein a first stimulation level of the second stimulation signal corresponds to the first strain value, and a second stimulation level of the second stimulation signal corresponds to the second strain value;
delivering the first stimulation signal to the first implantable electrode; and
delivering the second stimulation signal to the second implantable electrode,
wherein the first stimulation signal and the second stimulation signal are coordinated, and
wherein the first stimulation signal has a series of first stimulation cycles each including a first stimulation period and a first non-stimulation period, the second stimulation signal has a series of second stimulation cycles each including a second stimulation period and a second non-stimulation period.

20. The method of claim 19, further comprising:
controlling one or more first stimulation parameters for the first stimulation signal; and
controlling one or more second stimulation parameters for the second stimulation signal.

21. The method of claim 20, wherein the one or more first stimulation parameters and the one or more second stimulation parameters each include one or more of an amplitude, a frequency, a pulse width, a rate of amplitude change, and a duty cycle.

22. The method of claim 19, wherein the first implantable electrode is configured to deliver the first stimulation signal proximate to a hypoglossal nerve to stimulate the hypoglossal nerve and activate at least one tongue muscle.

23. The method of claim 22, wherein delivering the first stimulation signal further comprises delivering the first stimulation signal proximate to one or more medial branches of the hypoglossal nerve (m-XII) to stimulate the one or more medial branches and activate one or more protrusion muscles of the at least one tongue muscle including genioglossus.

24. The method of claim 19, wherein the second implantable electrode is configured to deliver a second stimulation signal proximate to an ansa cervicalis nerve to stimulate the ansa cervicalis nerve and activate one or more infrahyoid muscles.

25. The method of claim 24, wherein the second stimulation signal is further configured to activate sternothyroid and sternohyoid simultaneously.

26. The method of claim 24, wherein modulating the second stimulation signal to activate the at least one second muscle further comprises modulating the second stimulation signal to activate the one or more infrahyoid muscles within the strain range between the first strain value and the second strain value, wherein a first amplitude level of the second stimulation signal corresponds to the first strain value, and a second amplitude level of the second stimulation signal corresponds to the second strain value.

27. The method of claim 19, further comprising controlling operation of a stimulation signal generator in a first mode, wherein the stimulation signal generator is configured to synchronize the first stimulation periods and the first non-stimulation periods of the first stimulation signal with the second stimulation periods and the second non-stimulation periods of the second stimulation signal, respectively.

28. The method of claim 19, further comprising controlling operation of a stimulation signal generator in a second mode, wherein a first duration of the first stimulation period is two or more times greater than a second duration of the second stimulation period.

29. The method of claim 19, further comprising coordinating the delivery of the first stimulation signal and the delivery of the second stimulation signal based at least in part on a historical respiratory waveform of the person.

30. The method of claim 29, further comprising synchronizing the series of first stimulation cycles of the first stimulation signal with a current respiratory waveform of the person.

* * * * *